(12) United States Patent
Lian et al.

(10) Patent No.: US 7,899,520 B2
(45) Date of Patent: Mar. 1, 2011

(54) MEDICAL DEVICE FOR MONITORING BIOLOGICAL SIGNALS

(75) Inventors: Jie Lian, Beaverton, OR (US); Garth Garner, Tigard, OR (US); Dirk Muessig, West Linn, OR (US); Volker Lang, West Linn, OR (US)

(73) Assignee: BIOTRONIK CRM Patent AG (CH)

( * ) Notice: Subject to any disclaimer, the term of this patent is extended or adjusted under 35 U.S.C. 154(b) by 373 days.

(21) Appl. No.: 12/124,499

(22) Filed: May 21, 2008

(65) Prior Publication Data

US 2008/0294217 A1 Nov. 27, 2008

Related U.S. Application Data

(60) Provisional application No. 60/939,096, filed on May 21, 2007, now abandoned, provisional application No. 60/939,097, filed on May 21, 2007, now abandoned.

(51) Int. Cl.
*A61B 5/04* (2006.01)
(52) U.S. Cl. ...................................... 600/509
(58) Field of Classification Search ................ 600/301, 600/521, 27, 509; 607/9, 28
See application file for complete search history.

(56) References Cited

U.S. PATENT DOCUMENTS

| | | | |
|---|---|---|---|
| 6,324,427 B1 | 11/2001 | Florio | |
| 7,006,869 B2 | 2/2006 | Bradley | |
| 7,086,603 B2 | 8/2006 | Florio et al. | |
| 7,123,963 B2 * | 10/2006 | Sawchuk et al. | 607/27 |
| 7,139,610 B2 | 11/2006 | Ferek-Petric | |
| 7,162,301 B2 | 1/2007 | Kim et al. | |
| 7,177,689 B2 | 2/2007 | Ternes et al. | |

* cited by examiner

*Primary Examiner*—George Manuel
*Assistant Examiner*—Robert N Wieland
(74) *Attorney, Agent, or Firm*—Craig A. Fieschko, Esq.; DeWitt Ross & Stevens S.C.

(57) ABSTRACT

A medical device having a sensor for sampling a biological signal, the biological signal representing a signal waveform and forming a waveform vector composed of the biological signal samples, and a memory for storing a least two threshold vectors composed of boundary samples representing at least two boundaries related to the biological signal defining subspaces for the biological signal samples. One threshold vector is an upper threshold vector composed of upper boundary samples and the other threshold vector is a lower threshold vector composed of lower boundary samples. An evaluation unit connected to the sensor determines a similarity index (ASCI) by comparing each of the biological signal samples of the waveform vector to corresponding boundary samples of the threshold vectors, thus determining to which subspace each biological signal sample belongs to and creating a trichotomized signal vector, and calculating the signed correlation product of two trichotomized signal vectors.

19 Claims, 25 Drawing Sheets

MEDICAL DEVICE FOR MONITORING BIOLOGICAL SIGNALS

CROSS-REFERENCE TO RELATED APPLICATIONS

This application claims priority under 35 USC §119(e) to U.S. Provisional Patent Applications 60/939,096 and 60/939,097, both filed 21 May 2007, now abandoned the entireties of which are incorporated by reference herein.

FIELD OF THE INVENTION

The present invention generally relates to medical devices and systems that incorporate components or methods to compare biological signals and to measure the similarity between biological signals.

The present invention particularly relates to implantable cardiac devices, including pacemakers, defibrillators and cardiovertors, which stimulate cardiac tissue electrically to control the patient's heart rhythm. More particularly, the present invention relates to a method and apparatus for capture detection of the heart by electrical stimulation of the heart, and adjusting stimulation signal thresholds for energy efficiency of the devices. Although the present invention is described in the context of three-chamber (RA, RV, LV) pacemaker/ICD devices, the same concept also applies to single chamber (RA or RV only), dual-chamber (RA and RV), or four-chamber (RA, LA, RV, LV) devices.

BACKGROUND

Biological signal is a general term that refers to the signal generated by a biological system. Depending on the measurement devices and recording methods in question, biological signals can take a variety of forms. One common type of biological signal is the bioelectric signal generated by the biological organs, tissues, or cells, for example, the body surface electrocardiogram (ECG) signal, the intracardiac electrogram (IEGM) signal, the scalp electroencephalogram (EEG) signal, the intracranial electrocorticogram (ECOG) signal, the electromyogram (EMG) signal, the gastric and intestinal electrogram, the somatosensory evoked potential (visual, auditory, motor) signal, neuronal or cellular action potential signal, etc. Another common type of biological signal is the impedance signal that is derived from voltage measurement after injecting a current to the biological tissue, for example, the intracardiac impedance signal, the thranstho-racic (across lung) impedance signal, etc. Yet another common type of biological signal is the pressure signal within a biological compartment, for example, the intracardiac (atrial and ventricular) blood pressure, the central and peripheral blood pressure, the intra-bladder pressure, the intra-uterine pressure, the intra-gastric pressure, the intra-cranial pressure, partial gas (e.g., oxygen) pressure, etc. Other types of biological signals include acoustic signals (e.g., heart sound, intracardiac or thransthoracic ultrasonic measurement, output of acoustic sensor in cochlea implant, etc.), temperature signals (e.g., core and peripheral body temperature, organ temperature), volume signals (e.g., cardiac output, cardiac stroke volume, respiratory tidal volume, etc.), chemical signals (e.g., glucose concentration, drug concentration, the pH level, etc.), event frequency signals (e.g., heart rate, respiration frequency, firing rate of action potentials, etc.), movement signals (e.g., accelerometer output, posture measurement, gait measurement), body weight signals, and so on. In addition, these directly measured biological signals can be further processed to generate secondary biological signals, for example, a composite signal derived from multiple measured biological signals, a frequency spectrum calculated from the measured time-domain signals, and so on.

Many biological signals show periodic variations. For example, the cardiac signal and blood pressure signal vary with heart beat cycles, the pulmonary signals vary with respiratory cycles, and many other biological signals show circadian variations. Even without apparent periodic variations, some biological signals show distinctive waveform morphology. Some representative examples include the myocardial evoked potentials after cardiac pacing, the somatosensory evoked potentials after external stimuli, the action potentials of neural or muscle cells, etc. These distinctive signal patterns reflect the dynamics of the biological systems. Therefore, useful information regarding the status of the biological systems can be probed by analyzing these signals patterns.

Numerous medical devices and systems have been developed to measure various types of biological signals by using different types of sensors. A common feature of these medical devices and systems is to provide diagnostic information regarding the biological system by analyzing the biological signals. Another common feature is to deliver appropriate therapies to the biological system according to the results of biological signal analysis. Therefore, accurate and efficient biological signal analysis is crucial for the normal operation of the medical devices and systems. Due to the distinctive patterns of many biological signals, one typical biological signal analysis technique is correlation analysis, which quantitatively measures the association between two signals. It has numerous applications, including morphological analysis, signal classification, pattern recognition, and so on.

One application of signal classification is capture detection or verification by recognizing a characteristic electrogram waveform after delivery of an electrical stimulation pulse (pace).

Implantable pulse generators (IPGs) such as pacemakers or defibrillators/cardioverters (ICD) can help ensure proper contractions of one or more heart chambers if proper natural contraction of the heart chambers is affected by a disease. A contraction of a heart chamber can be induced by an electrical stimulation pulse generated by an IPG. Depending on the chambers of a heart to be stimulated, single, dual or more chamber pacemakers, e.g. three chamber biventricular pacemakers, are known.

In a healthy heart, initiation of the cardiac cycle normally begins with depolarization of the sinoatrial (SA) node. This specialized structure is located in the upper portion of the right atrium wall and acts as a natural "pacemaker" of the heart. In a normal cardiac cycle and in response to the initiating SA depolarization, the atrium contracts and forces the blood that has accumulated therein into the ventricle. The natural stimulus causing the atrium to contract is conducted to the ventricle via the atrioventricular (AV) node with a short, natural delay, the atrioventricular delay (AV-delay). Thus, a short time after an atrial contraction (a time sufficient to allow the bulk of the blood in the atrium to flow through the one-way valve into the ventricle), the ventricle contracts, forcing the blood out of the ventricle to body tissue. A typical time interval between contraction of the atrium and contraction of the ventricle might be 180 ms; a typical time interval between contraction of the ventricle and the next contraction of the atrium might be 800 ms. Thus, in a healthy heart providing proper AV-synchrony, an atrial contraction (A) is followed a relatively short time thereafter by a ventricle contraction (V), that in turn is followed a relatively long time thereafter by the next atrial contraction and so on.

To mimic the natural behavior of a heart, a dual-chamber pacemaker, in conventional manner, defines a basic atrial escape interval (AEI) that sets the time interval for scheduling an atrial stimulation pulse. The atrial escape interval can be started by a ventricular event and end with an atrial event. A basic AV delay (AVD) or ventricular escape interval (VEI) sets the time interval or delay between an atrial event and a ventricular event. In such embodiment, AEI and AVD (or VEI) thus together define a length of a heart cycle which is reciprocal to the pacing rate at which stimulation pulses are generated and delivered to a patient's heart in the absence of sensed natural cardiac activity.

Depending on the mode of operation, a pacemaker only delivers a stimulation pulse (pacing pulse) to a heart chamber (atrium or ventricle) if needed, that is, if no natural excitation of that chamber occurs. Such mode of operation is called an inhibited or demand mode of operation since the delivery of a stimulation pulse is inhibited if a natural excitation of the heart chamber is sensed within a predetermined time interval (usually called escape interval) so the heart chamber is only stimulated if demanded.

In a demand mode, the pacemakers monitors the heart chamber to be stimulated in order to determine if a cardiac excitation (heartbeat) has naturally occurred. Such natural (non-stimulated) excitation, also referred to as "intrinsic" cardiac activity, is manifested by the occurrence of recognizable electrical signals that accompany the depolarization or excitation of a cardiac muscle tissue (myocardium). The depolarization of the myocardium is usually immediately followed by a cardiac contraction. For the purpose of the present application, depolarization and contraction may be considered as coupled events and the terms "depolarization" and "contraction" are used herein as synonyms. The recognizable electrical signals that accompany the depolarization or excitation of a heart chamber are picked up (sensed) by the atrial or the ventricular sensing channel, respectively. Thus, one or more intracardiac electrograms (IEGMs) are acquired.

After delivery of a successful stimulation pulse a characteristic electrical signal can be recorded, called the evoked response. After delivery of an unsuccessful stimulation pulse not leading to capture, no evoked response can be recorded (apart from a different characteristic electrical signal called the polarization artifact.)

A natural contraction of a heart chamber can also be detected by evaluating electrical signals sensed by the sensing channels. In the sensed electrical signal the depolarization of an atrium muscle tissue is manifested by occurrence of a signal known as "P-wave". Similarly, the depolarization of ventricular muscle tissue is manifested by the occurrence of a signal known as "R-wave". A P-wave or a R-wave represents an atrial event or a ventricular event, respectively, in the further course of this application.

For the purpose of this application, a "ventricular event" (V) may refer either a natural ventricular excitation (intrinsic ventricular event; Vs) which is sensed as an R-wave or a ventricular stimulation pulse (V-pulse, Vp). Similarly, an atrial event (A) shall refer to both a P-wave (A-sense; As) or an atrial stimulation pulse (A-pulse, Ap).

An implantable cardiac device, particularly an artificial cardiac pacemaker, "captures" the heart by delivering an appropriately timed electrical pulse designed to cause contraction of the myocardium of the heart. To ensure capture, the strength and duration of the stimulation pulse should be adjusted so that the energy being delivered to the myocardium exceeds a threshold value. On the other hand, it is desirable for the pulse energy not to be higher than is needed for a reasonable safety margin for longer battery life. Because the threshold for capture varies from patient to patient, and can change over time for the same patient, it is also desirable that the pulse energy delivered by the pacemaker be adjustable during and subsequent to implantation. Although periodic adjustment can be made manually through use of an external programmer that communicates with the implanted pacemaker, it would be preferable to provide a pacemaker that adjusts the pulse energy automatically and dynamically in response to changes in the capture threshold. This functionality requires the pacemaker to be able to verify capture after the delivery of pacing pulse, and has the capability of automatically testing the capture threshold.

Many different approaches have been taken during the past decade to develop the pacemakers with "auto-capture control" functionality. Theoretically, capture verification could be accomplished by detecting the existence of evoked potential that manifests in a characteristic ECG waveform, which should follow a capturing pulse but not the non-capturing pulse. In practice, however, reliable detection of the evoked potential is quite challenging because the after-potentials and electrode-tissue polarization artifacts resulting from the pacing pulse mask the evoked response and change the ECG waveform, and also saturate the sense amplifiers coupled to the electrodes, until they dissipate. By the time that the sense amplifier is no longer blinded, the evoked response, if any, has typically passed the electrodes.

Because of these technical difficulties, so far there has been only limited success in beat-by-beat capture classification for RV pacing based on evoked potential analysis. For the RA pacing, and for the RV and LV pacing in the CRT and CRT/D devices, currently there is no solution that can perform capture classification on a beat-by-beat basis.

Atrial capture detection based on evoked potential analysis is technically more challenging than RV capture detection because the amplitude of the atrial evoked potential is much smaller and more difficult to discriminate from noise, other cardiac signals, and the residual polarization charge on the electrode.

For CRT (cardiac resynchronization therapy) and CRT-D/ CRT+ defibrillator devices, the RV and LV capture detection based on evoked potential analysis is also difficult, particularly when the device is programmed with a V-V delay not equal to zero. Each ventricular pace not only triggers a blanking window (during which ECG signals are either not recorded or ignored) in the same ventricular channel, but also starts a blanking window (cross-channel blanking) in the other ventricular channel. As a result, the non-blanked ventricular electrogram that is available for analysis has shortened duration, and the evoked potential waveform, which is crucial for capture detection, is often blanked.

Furthermore, it has been known that the RV capture detection based on evoked potential analysis (waveform of the ECG after stimulation pulse delivery) can be negatively affected by the ventricular fusion (simultaneous occurrence of RV pace and the antegrade conducted wave). For the CRT and CRT/D devices, the fusion beat poses a more challenging problem for the capture detection, because one ventricle chamber not only can be activated by pacing, it may also be activated by the wave conducted from the other ventricle chamber.

Instead of solely relying on evoked potential analysis for capture classification, alternative methods have been developed to analyze the pace waveform, possibly including part of the T wave, for capture classification (U.S. Pat. Nos. 6,324, 427, 7,006,869, 7,086,603, 7,139,610, 7,162,301, 7,177,689). Generally, the template waveform corresponding to captured beats is created. Capture is declared if a paced signal waveform matches the template, otherwise, non-capture is declared. Whether or not a waveform matches the template can be evaluated based on simple morphological metrics such as wave width, height, zero-crossing, area, etc., or based on conventional correlation analysis techniques, such as the Pearson's correlation coefficient (see below). However, all these methods are not suitable for implementation in the implant device due to many limitations. For example, the template waveform may be contaminated by the pacing artifacts caused by paces from one or multiple chambers; the template waveform may not be comparable to the test waveform due to different device parameter settings, such as various V-V delays and pace blanking periods; the methods used for assessing similarity between template waveform and test waveform either have low sensitivity and specificity (e.g., morphological metrics), or require high computational cost (e.g., Pearson's correlation coefficient); and furthermore, there is lack of strategy regarding how the implant device shall automatically and rationally manage its operation based on continuous capture classification.

Thus there is a need for the implant device to implement an integrated yet efficient strategy, to continuously monitor the pacing capture status in all three chambers (RA, RV, LV), to confirm the pacing capture, to detect non-capture paces, and accordingly adjust the pacing parameters to ensure capture.

One of the most commonly used indices for correlation analysis is the Pearson's correlation coefficient (CC), which provides a quantitative measure of the linear relationship between two signals (one-dimensional, two-dimensional, or multi-dimensional). Considering $X=[x1, x2, \ldots, x_L]$ and $Y=[y1, y2, \ldots, y_L]$ are two one-dimensional vectors of length L, and each has zero mean, their CC is defined as:

$$CC = \frac{X \cdot Y}{\|X\| \cdot \|Y\|} = \frac{\sum_{i=1}^{L} x_i \cdot y_i}{\sqrt{\sum_{i=1}^{L} x_i^2} \cdot \sqrt{\sum_{i=1}^{L} y_i^2}}$$

The CC approaches 1 when there is a positive linear relationship between X and Y, approaches −1 when there is a negative linear relationship between X and Y, and is some value in between otherwise, indicating the degree of linear dependence between the two vectors. Consequently, the CC has been frequently used to quantify the similarity between two signals. That is, two signals X and Y are considered increasingly similar when their CC is approaching 1. Conversely, X and Y are considered not similar for decreasing CC, and in opposite phase when their CC is −1.

However, there are several limitations for using CC as a measure of signal similarity. First, the calculation of CC usually requires extensive floating-point operation, which renders it impractical for implementation in low-power devices or systems such as battery-powered implantable medical devices. Second, the CC is less sensitive to amplitude discrepancy between the signals. For example, the CC between two signals X and $Y=\rho \cdot X$, where $\rho$ is a constant scaling factor, is always 1, despite the fact that the amplitude of Y can be significantly different than that of X. Thirdly, the CC between two signals is affected by each sample amplitude of each signal, and thus is sensitive to additive noise such as impulse noise or continuous random noise.

Therefore, there is a need for a new methods and devices for quantitatively, efficiently, and robustly measuring the similarity between biological signals.

SUMMARY OF THE INVENTION

The invention involves a method for quantifying the similarity between two signals. The new method is based on calculation of an Adaptive Signed Correlation Index (ASCI) between two signals, e.g. a measured test signal and a template signal, that can be a measured signal itself. The ASCI is calculated by trichotomizing each signal based on three signal subspaces that are defined from the template signal, and calculating the signed correlation product of the two trichotomized signals. Exemplary embodiments on software and hardware implementation of the ASCI are presented.

The signals to be compared are represented by signal waveform vectors composed of signal samples recorded e.g. by a sensing stage.

In addition, this invention provides a novel strategy for automatic three-chamber (RA, RV, LV) continuous capture management.

According to this invention, a template waveform representing an IEGM waveform after a captured stimulation pulse is created for each specific pace/sense configuration of the corresponding heart chamber configurations that differ from each other e.g. by electrode configuration or the stimulated heart chamber. Each template waveform spans from the early evoked potential to the repolarization phase of the IEGM. The template waveform can also be continuously updated after each confirmed captured pace.

For capture verification a test waveform is compared to a template waveform. Similarity is determined by calculating the ASCI. Both the test waveform and the template waveform are represented by waveform vectors as defined above.

According to this invention, both template waveform vector and the test post-pace waveform vector are trichotomized based on the adaptive baseline zone that has varying threshold. The Adaptive Signed Correlation Index (ASCI) is defined to quantitatively measure the similarity between two trichotomized waveforms.

Segments of waveforms corresponding to the post-pace blanking periods are masked and excluded from calculating the similarity index ASCI.

According to this invention, for each chamber, the implant device continuously calculates the ASCI between a test post-pace IEGM waveform and the corresponding template waveform. If ASCI is greater than a predefined/user-programmable threshold, then capture is confirmed. Otherwise, non-capture is suspected.

According to a preferred embodiment of this invention, a three-chamber capture management protocol for an implantable heart stimulator's control unit is developed. The protocol defines multiple states and contains an algorithm that controls the transition between these states. During normal operation, the implantable heart stimulator remains in the monitoring state and checks the capture status on a beat-by-beat basis in each chamber. If non-capture status is suspected in a specific chamber, the operation transits to different states for further testing, to check if the non-capture is caused by sub-threshold pacing, or caused by inappropriate parameter setting (e.g., AV delay or VV delay), or is just an incidental event. According to the test results, appropriate actions are triggered, for example, to trigger a threshold search and/or adjust the pacing amplitude, and/or to adjust the device parameters, etc.

Also according to a preferred embodiment of this invention, the implantable heart stimulator maintains an event log and collects statistics periodically when running the above protocol. These event logs and statistics are transmitted through wired or wireless network to the remote service center, providing important diagnostic information regarding the patient's cardiac condition (e.g., threshold change), and the device condition (e.g., inappropriate AV or VV delay settings).

In particular, the object of the invention is addressed by a medical device comprising

- at least one sensor for acquiring and sampling a biological signal,
- an evaluation unit that is connected to the sensor for receiving a plurality of samples of the biological signal representing a signal waveform and forming a waveform vector composed of the biological signal samples, and
- a memory for storing at least two threshold vectors composed of boundary samples representing at least two boundaries related to the biological signal defining subspaces for biological signal samples, wherein one threshold vector is an upper threshold vector composed of upper boundary samples and the other threshold vector is a lower threshold vector composed of lower boundary samples, wherein each lower boundary sample is less than or equal to the corresponding upper boundary sample.

The evaluation unit is adapted to determine a similarity index (ASCI) by trichotomizing the waveform vector by comparing each of the biological signal samples of the waveform vector to corresponding boundary samples of the threshold vectors, thus determining to which subspace each biological signal sample belongs to and creating a trichotomized signal vector, and calculating the signed correlation product of two trichotomized signal vectors.

Preferably, the evaluation unit is adapted

- to determine a positive threshold vector and a negative threshold vector which together define an adaptive threshold zone (ABZ) and
- to determine a similarity index (ASCI) by trichotomizing two waveform vectors based on the threshold vectors;

calculating the signed correlation product between each sample pair of the two waveform vectors;

calculating a signed correlation product between the two waveform vectors by summing the signed correlation products of all sample pairs; and normalizing the signed correlation product between the two waveform vectors by the total count of biological signal sample pairs, thereby preferably ignoring biological signal samples corresponding to a blanking period.

The evaluation unit can be adapted to trichotomize a waveform vector by:

comparing each biological signal sample of the waveform vector to the adaptive threshold vectors;

setting the biological signal sample's trichotomized value to +1 if the biological signal sample is greater than the corresponding upper boundary sample;

setting the biological signal sample's trichotomized value to −1 if the biological signal sample is less than the corresponding lower boundary sample;

setting the biological signal sample's trichotomized value to 0 if the biological signal sample is less than or equal to the corresponding upper boundary sample, but greater than or equal to the corresponding lower boundary sample.

With respect to determination of the signed correlation product of two trichotomized waveform vectors, the evaluation unit may be adapted for:

taking one biological signal sample from a first vector and taking a corresponding biological signal sample from the second waveform vector thus forming a biological signal sample pair, setting the sample biological signal pair's signed correlation product output to +1 if both biological signal samples are greater than the corresponding upper boundary sample, or both biological signal samples are less than the corresponding boundary sample, or both samples are greater than or equal to the corresponding lower boundary sample and less than or equal to the corresponding upper boundary sample;

setting the biological signal sample pair's signed correlation product output to −1 if one of the biological signal samples is greater than the corresponding upper boundary sample, whereas the other biological signal sample is less than the corresponding lower boundary sample;

setting the biological signal sample pair's signed correlation product output to 0 if one of the biological signal samples is greater than or equal to the corresponding lower boundary sample and less than or equal to the corresponding upper boundary sample, whereas the other sample is either greater than the corresponding upper boundary sample or less than the corresponding lower boundary sample.

In a preferred embodiment, the evaluation unit is adapted to determine a template waveform vector and to store the template waveform vector for later determination of a similarity index (ASCI) for the template waveform vector and a test waveform vector.

The medical device preferably is an implantable pulse generator such as a cardiac pacemaker and/or cardioverter/defibrillator comprising

- at least one stimulation pulse generator adapted to generate electric stimulation pulses and being connected or being connectable to at least a stimulation electrode for delivering electric stimulation pulses to at least one chamber of a heart,
- at least one sensing stage connected or being connectable to an electrode for picking up electric potentials inside at least the chamber of a heart, the sensing stage being adapted to record at least a portion of an intracardiac electrogram (IEGM) in the heart chamber, and
- a control unit that is connected to the stimulation pulse generator and the sensing stage and that is adapted to trigger generation of stimulation pulses by the stimulation pulse generator.

The evaluation unit is adapted

- to determine a capture template waveform vector from at least one IEGM portion representing an evoked response after successful stimulation of a heart chamber,
- to store the template waveform,
- to generate a test waveform vector from an actual IEGM portion after a delivery of stimulation pulse to the heart chamber,
- to determine a similarity index (ASCI) for the template waveform vector and the test waveform vector according to claim 1 or 2, and
- determine capture or loss of capture based on whether or not the similarity index thus determined for the test waveform exceeds a preset threshold value or not, respectively.

The control unit preferably is adapted
- to trigger generation of stimulation pulses with an overdrive stimulation rate exceeding an intrinsic heart rate as determined via the sensing stage to thus ensure that a stimulation pulse is triggered before an intrinsic event occurs, and
- to sample a post stimulation pulse intracardiac electrogram after each stimulation pulse generated with the overdrive stimulation rate thus acquired a sequence of biological signal samples forming a waveform vector.

The control unit may temporarily change device parameters to ensure effective overdrive pacing in the corresponding chamber (for RA chamber, shorten the AP coupling interval and program the max AP amplitude; for RV and LV chamber, program short AVD and program max RVP and LVP amplitudes).

The evaluation unit preferably is adapted
- to collect waveform vectors for consecutive N cycles by sampling N post stimulation pulse intracradic electrograms of the corresponding heart chamber;
- to calculate the similarity index (ASCI) between each pair of biological signal samples of the collected waveform vectors; and
- to generate the template waveform vector by averaging all N collected waveform vectors if the calculated ASCI of all N(N+1)/2 pairs are greater than a predefined threshold.

Preferably, the evaluation unit is adapted to update the template vector on a beat-by-beat basis.

The evaluation unit is adapted to automatically define the upper threshold vector by:
- setting the boundary samples of the upper threshold vector and the lower threshold vector to 0 for a first post-stimulation pulse segment;
- setting the boundary samples of the upper threshold vector to one half of the largest sample of the post stimulation pulse intracardiac electrogram for the second post stimulation pulse segment; and
- setting the boundary samples of the upper threshold vector to one quarter of the largest sample of the post stimulation pulse intracardiac electrogram for the third post stimulation pulse segment.

Similarly, the evaluation unit may be adapted to automatically define the lower threshold vector by:
- setting the boundary samples of the lower threshold vector to 0 for a first post-stimulation pulse segment;
- setting the boundary samples of the lower threshold vector to a negative value of one half of the largest sample of the post stimulation pulse intracardiac electrogram for the second post stimulation pulse segment; and
- setting the boundary samples of the lower threshold vector to a negative value one quarter of the largest sample of the post stimulation pulse intracardiac electrogram for the third post stimulation pulse segment.

Alternatively, the evaluation unit may be adapted to define the upper threshold vector and the lower threshold vector sample-by-sample from a template threshold vector.

This can be achieved by an evaluation unit that is adapted to define the upper threshold vector and the lower threshold vector by adding a positive offset value and a negative offset value, respectively, to some or each signal sample of the template waveform vector to thus generate an upper boundary sample and a lower boundary sample respectively.

This can alternatively be achieved by an evaluation unit that is adapted to define the upper threshold vector and the lower threshold vector by scaling some or each signal sample of the template waveform vector by a factor greater than 1 and a factor less than one, respectively, to generate an upper boundary sample and a lower boundary sample respectively.

The evaluation unit may be adapted to determine a capture status for a stimulation pulse by
- calculating the similarity index (ASCI) between a test waveform vector and a corresponding template waveform vector, wherein the test waveform vector is generated after delivery of the stimulation pulse by sampling an according post stimulation pulse intracardiac electrogram; and
- confirming capture if the similarity index (ASCI) between the test waveform vector and the template waveform vector is greater than a predefined threshold.

Preferably, the evaluation unit is adapted to update the template waveform vector to the sum of pre-update template waveform vector scaled by 255/256, and the test waveform vector for which capture has been confirmed scaled by 1/256.

With respect to template waveform updating, it is preferred that the evaluation unit is adapted to ignore biological signal samples of template waveform vectors that correspond to a blanking window.

As already pointed out above, the similarity index (ASCI) can be used for capture monitoring of more than one pacing configuration including different electrode configurations and/or different heart chambers to be stimulated. This is preferably achieved by:
- constructing and maintaining a template waveform vector representing a sampled intracardiac electrogram after successful stimulation of a heart chamber for each specific pace and sense configuration of the heart chamber;
- calculating the similarity index (ASCI) between a post-stimulation pulse test waveform and the corresponding template waveform;
- confirming capture if the similarity index (ASCI) between the test waveform vector and the template waveform vector for the pace for the pace configuration used for generating the test waveform vector is greater than a threshold;
- declaring non-capture if the similarity index (ASCI) between the test waveform vector and the template waveform vector for the pace configuration used for generating the test waveform vector is less than the threshold.

In particular, a right atrial capture management can be achieved by:
- operating in MONITOR_STATE to monitor a capture status of each right atrial stimulation pulse by evaluating the similarity index (ASCI) between a post atrial stimulation pulse test waveform vector and a corresponding atrial stimulation template waveform vector;
- transiting from MONITOR_STATE to SHORT_STATE by temporarily shortening an atrial coupling interval (AAp interval or VAp interval), if 3 out of 4 right atrial stimulation pulses are classified as non-capture;
- declaring loss-of-capture if non-capture status is detected in the SHORT_STATE, and triggering a pacing threshold search to determine the RA pacing threshold, and adjusting a right atrial stimulation pulse strength accordingly to ensure subsequent right atrial capture; and
- returning to MONITOR_STATE if capture is confirmed in the SHORT_STATE.

Similarly, automatic capture management in a right ventricle and a left ventricle can be achieved by:
- operating in MONITOR_STATE to monitor a capture status of each right ventricular stimulation pulse and left ventricular stimulation pulse by evaluating a similarity index (ASCI) between a post stimulation pulse test waveform vector and the corresponding template waveform vector, and confirming capture if capture is confirmed for both, the right ventricular stimulation pulse and the left ventricular stimulation pulse, and declaring non-capture if non-capture is declared for either, the right ventricular stimulation pulse or the left ventricular stimulation pulse;

transiting from MONITOR_STATE to SHORT_STATE by temporarily shortening an atrioventricular delay to 50 ms and setting an interventricular delay to 0 ms, if for 2 out 3 right ventricular stimulation pulses right or left ventricular stimulation pulses non-capture has been declared;

declaring loss-of-capture if non-capture is declared in the SHORT_STATE, and triggering a capture threshold search to determine a minimum required stimulation pulse strength in the suspected right ventricle or left ventricle or both, and adjusting the stimulation pulse strength accordingly to ensure subsequent capture of stimulation pulses;

transiting to AV_CHECK_STATUS by restoring an original atrioventricular delay while maintaining the interventricular delay of 0 ms, if capture is confirmed for 2 consecutive stimulated heart cycles in SHORT_STATE;

transiting back to SHORT_STATE if non-capture is declared in the AV_CHECK_STATE and such back-transition does not occur for 3 consecutive times;

decreasing the atrioventricular delay by a predefined interval if the state transition from AV_CHECK_STATE to SHORT_STATE occurs for 3 consecutive times;

limiting the decrement of the atrioventricular delay by a predefined minimum atrioventricular delay, and returning to the MONITOR_STATE;

transiting to SUSPENDED_STATE by programming a maximum right ventricular stimulation pulse amplitude and a maximum left ventricular stimulation pulse amplitude, a minimum atrioventricular delay, and an interventricular delay of 0 ms, if the attempts to shorten the atrioventricular delay is limited by the minimum atrioventricular delay for multiple times within a day;

transiting to VV_CHECK_STATE by restoring the programmed interventricular delay value, if capture is confirmed for 2 consecutive stimulated heart cycles in the AV_CHECK_STATE;

changing the interventricular delay to 0 ms if non-capture is declared in the VV_CHECK_STATE, and returning to the MONITOR_STATE;

returning to MONITOR_STATE if capture is confirmed for consecutive 2 pace cycles in the VV_CHECK_STATE;

triggering threshold search periodically to determine the capture threshold for the right ventricle or the left ventricle or both, and adjust the stimulation pulse strength accordingly to ensure subsequent capture stimulation pulses; and restoring the programmed atrioventricular delay and interventricular delay periodically, or testing the programmed atrioventricular delay and interventricular delay periodically, and restoring the programmed atrioventricular delay and interventricular delay only if they result in confirming capture.

A further solution of the object of the invention is provided by a method of automatic capture management for more than one pacing configuration on a beat-by-beat basis. In one embodiment, the method includes the steps of:

constructing and maintaining a template waveform vector representing a sampled intracardiac electrogram after successful stimulation of a heart chamber for each specific pace and sense configuration of the heart chamber;

calculating the similarity index (ASCI) between a post-stimulation pulse test waveform and the corresponding template waveform;

confirming capture if the similarity index (ASCI) between the test waveform vector and the template waveform vector for the pace configuration used for generating the test waveform vector is greater than a threshold;

declaring non-capture if the similarity index (ASCI) between the test waveform vector and the template waveform vector for the pace configuration used for generating the test waveform vector is less than the threshold.

It is to be noted that features of the various embodiments above may be combined in any non self-contradictory manner, thus producing further embodiments not explicitly mentioned herein.

The details of the invention can be understood from the following drawings and the corresponding text descriptions.

DETAILED DESCRIPTION OF THE INVENTION

The details of the invention can be understood from the following drawings and the corresponding text descriptions. The following description is of the best mode presently contemplated for carrying out the invention. This description is not to be taken in a limiting sense, but is made merely for the purpose of describing the general principles of the invention. The scope of the invention should be determined with reference to the claims.

Biological Signal Acquisition

Figure 1:
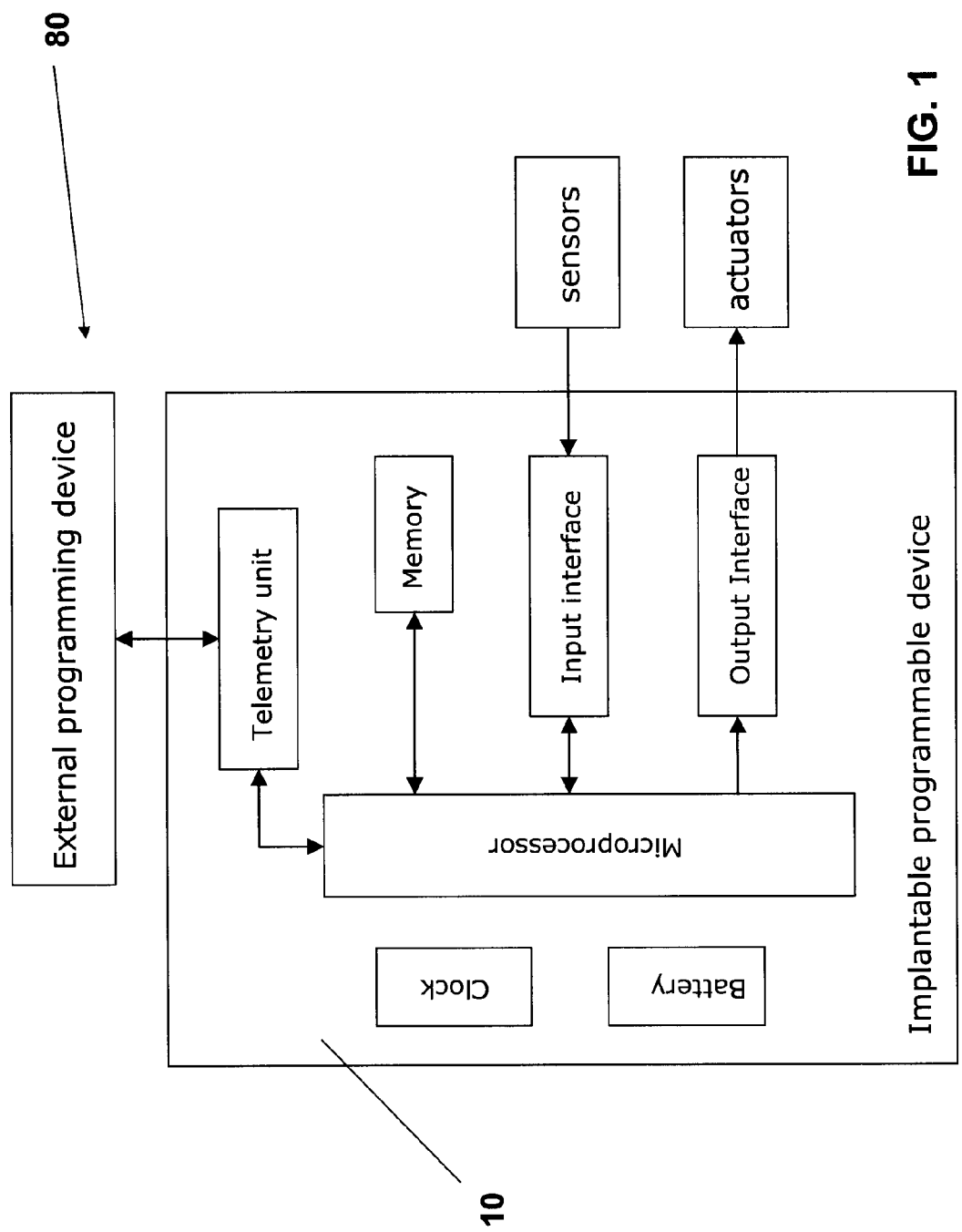
FIG. 1 is a simplified block diagram of a medical system.

Medical devices and systems are designed to measure and analyze various types of biological signals. For illustration purpose, FIG. 1 shows a simplified block diagram of a medical system that consists of two parts: one implantable programmable device (IPG) 10 and one external programming device (EPD) 80.

Typically, the IPG is a low-power device implanted within a patient to automatically acquire biological signals, analyze the biological signals, and may deliver therapy to the patient according to the results of biological signal analysis. Some representative IPGs include, but are not limited to, implantable cardiac pacemakers, implantable cardioverter-defibrillators, implantable drug pumps, implantable cortical stimulators, implantable deep brain stimulators, implantable spinal cord stimulators, implantable vagus nerve stimulators, implantable bladder controllers, implantable gastric stimulators, implantable physiological monitors (e.g., blood pressure, pH, glucose concentration, temperature, etc.), cochlear implants, retina implants, and so on.

An IPG is typically composed of a microprocessor and associated circuitry. The IPG is usually powered by a battery, which may or may not be rechargeable. The IPG also maintains a system clock that controls the timing of device operations. The microprocessor communicates with a memory via a bi-directional data bus. The memory typically comprises a ROM or RAM for program storage and a RAM for data storage.

The biological signals are usually acquired by one or more special sensors, which are also implanted in the patient's body. Typical sensors include, but are not limited to, electrical sensors, impedance sensors (including volume sensors), pressure sensors, temperature sensors, acoustic sensors, chemical sensors (including pH sensors), displacement or velocity sensors, etc. The acquired biological signals are sent to the IPG microprocessor through an input interface, which usually consists of analog filters, amplifiers, analog-to-digital converters (ADC), digital filters, and so on. By running the program stored in the memory, the microprocessor also sends instructions to the input interface to control how the biological signals are acquired (e.g., sampling frequency, sampling resolution, etc.). The acquired biological signals are then stored in the device memory and analyzed by the microprocessor by running programmed algorithms.

Based on the analysis results, the microprocessor can send instructions to an output interface, through which to control one or more actuators to deliver appropriate therapies to the patient. The output interface usually consists of digital filters, digital-to-analog converters (DAC), amplifiers, etc. Typical actuators include, but are not limited to, electrical stimulators (e.g., current injection, shock induction), vibrators, acoustic generators (e.g., radio frequency wave generator), thermoelectric generator, mechanical valves or pumps, and so on.

Typically, the IPG is arranged to communicate with an EPD through a telemetry unit, which is coupled to the IPG microprocessor over a bi-directional bus. The telemetry unit may be of the type well known in the art for conveying various information (e.g., measured biological signal, results of biological signal analysis, etc.), which it obtains from the microprocessor to the EPD, or for receiving programming instructions or parameters from the EPD and then conveys to the IPG microprocessor for storage in the IPG memory.

Figure 2:
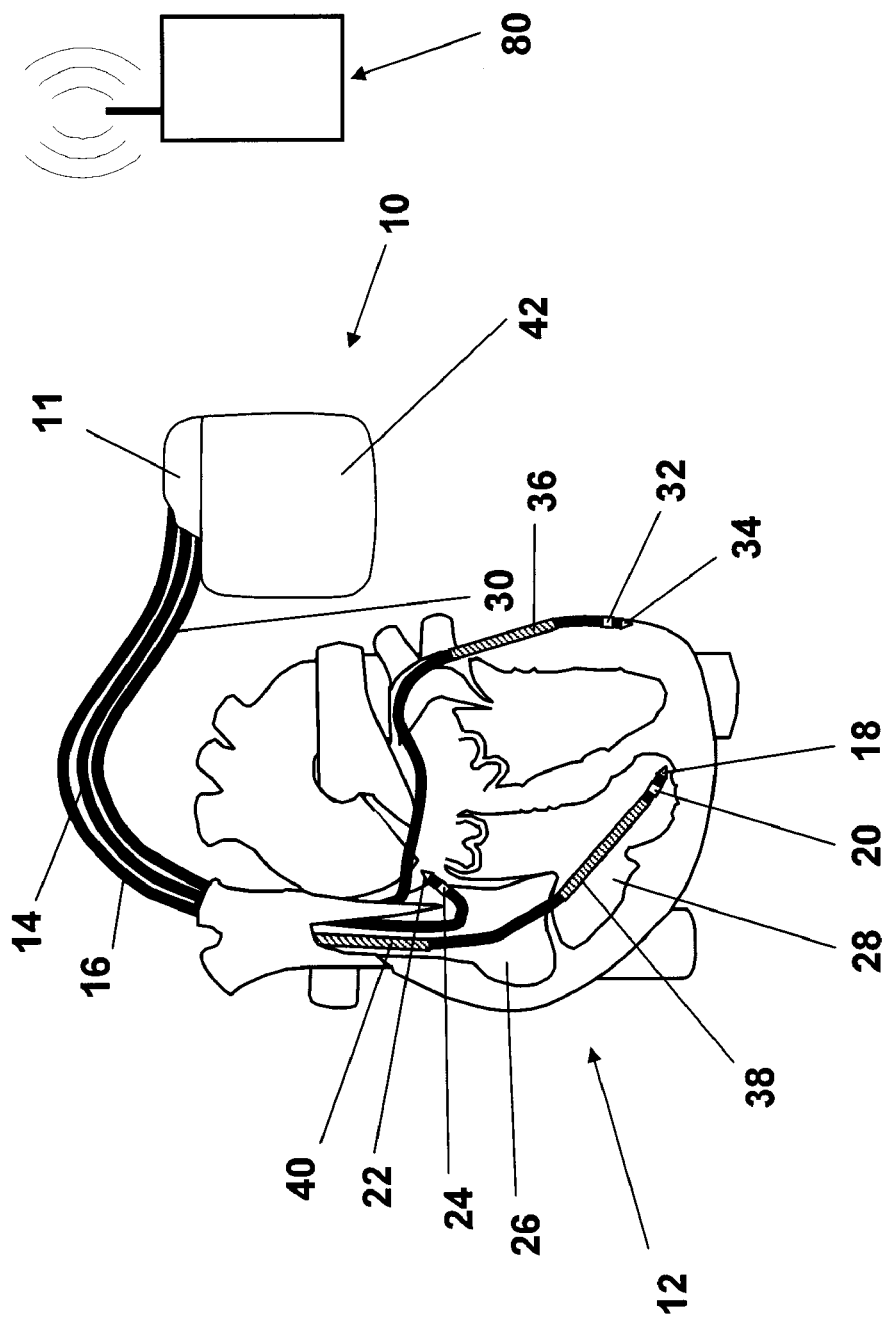
FIG. 2 is a schematic representation of an implantable 3 chamber heart stimulator.
Figure 3:
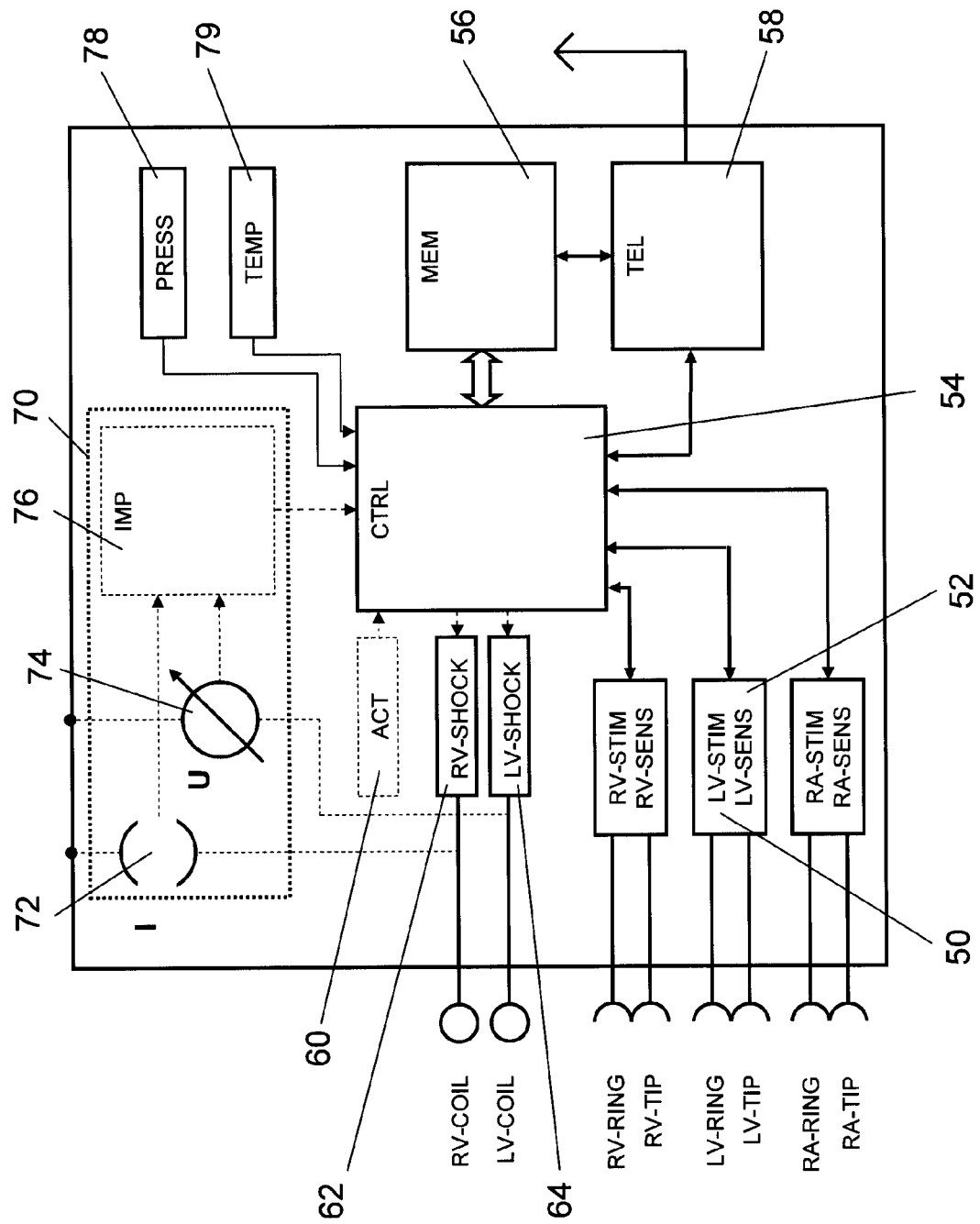
FIG. 3 is a simplified block diagram of the heart stimulator of FIG. 2.

A typical IPG is an implantable heart stimulator as illustrated with respect to FIGS. 2 and 3.

In FIG. 2 the implantable medical device is a three chamber biventricular pacemaker and cardioverter/defibrillator 10 that is connected to pacing/sensing leads placed in a heart 12 is illustrated.

Pacemaker 10 comprises a gas proof housing (case) 42 made from a biocompatible metal such as titanium. Pacemaker 10 comprises a transparent header 11 that is made from electrically insulating plastic and that encloses terminals to which electrode leads 16, 18 and 30 are detachably connected. Electrode leads 16, 18 and 30 each comprise a proximal connector (not shown) that is plugged into the connectors of header 13.

The implantable medical device 10 is electrically coupled to heart 12 by way of leads 14, 16 and 30.

Lead 14 is a right atrial lead that has a pair of right atrial electrodes 22 and 24 that are in contact with the right atrium 26 of the heart 12.

Lead 16 is a right ventricular lead that has a pair of ventricular stimulation and sensing electrodes 18 and 20 that are in contact with the right ventricle 28 of heart 12. Further, a ventricular defibrillation shock coil 38 and an atrial defibrillation shock coil 40 are arranged on lead 16.

Electrodes 22 and 18 are tip electrodes at the very distal end of leads 14 and 16, respectively. Electrode 22 is a right atrial tip electrode RA Tip and electrode 18 is a right ventricular tip electrode. Electrodes 24 and 20 are ring electrodes in close proximity but electrically isolated from the respective tip electrodes 22 and 18. Electrode 24 forms a right atrial ring electrode RA Ring and electrode 20 forms a right ventricular ring electrode RV Ring. Atrial cardioversion shock coil 40 is a coil electrode providing a relatively large geometric area when compared to the stimulation electrodes 18, 20, 22 and 24.

Lead 30 is a left ventricular lead passing through the coronary sinus of heart 12 and having a left ventricular ring electrode LV RING 32 a left ventricular tip electrode LV TIP 34. Further, a left ventricular defibrillation shock coil 36 is arranged on lead 30.

Implantable medical device 10 has a case 42 made from electrically conductive material such as titanium that can serve as a large surface electrode IMD case.

The plurality of electrodes 18, 20, 22, 24, 32, 34, 36, 38 and 40 connected to implantable medical device 10 together with case 42 allow for a number of different electrode configurations for measuring intrathoracic and intracardiac impedance.

Referring to FIG. 3 a simplified block diagram of an implantable medical device 10 is illustrated. During operation of the pacemaker leads 14, 16 and 30 are connected to respective output/input terminals of pacemaker 10 as indicated in FIG. 2 and carry stimulating pulses to the tip electrodes 18, 22 and 34 from a right ventricular pulse generator RV-STIM, a right atrial stimulation pulse generator RA-STIM and a left ventricular pulse generator LV-STIM, respectively. Further, electrical signals from the right ventricle are carried from the electrode pair 18 and 20, through the lead 16, to the input terminal of a right ventricular sensing stage RV-SENS; and electrical signals from the right atrium are carried from the electrode pair 22 and 24, through the lead 14, to the input terminal of a right atrial channel sensing stage RA-SENS. Electrical signals from the left ventricle are carried from the electrode pair 32 and 34, through the lead 30, to the input terminal of a right ventricular sensing stage RV-SENS.

The atrial channel sensing stage A-SENS and ventricular sensing stages RV-SENS and LV-SENS preferably include analog to digital converters (ADC; not shown) that generate a digital signal from electric signals picked up in the atrium or the ventricle, respectively.

Controlling the implantable medical device 10 is a control unit CTRL 54 that is connected to sensing stages A-SENS and V-SENS, to stimulation pulse generators A-STIM and V-STIM, and to an impedance determination unit 70. Control unit CTRL 54 comprises a digital microprocessor forming a central processing unit (CPU; not shown) and is—at least in part—controlled by a program stored in a memory circuit MEM 56 that is coupled to the control unit CTRL 54 over a suitable data/address bus ADR.

Control unit CTRL 54 receives the output signals from the atrial sensing stage RA-SENS and from the ventricular sensing stages RV-SENS and LV-SENS. The output signals of sensing stages RA-SENS and RV-SENS are generated each time that a P-wave representing an intrinsic atrial event or an R-wave representing an intrinsic ventricular event, respectively, is sensed within the heart 12. An As-signal is generated, when the atrial sensing stage RA-SENS detects a P-wave and a Vs-signal is generated, when the ventricular sensing stage RV-SENS detects an R-wave.

Control unit CTRL 54 also generates trigger signals that are sent to the atrial stimulation pulse generator RA-STIM and the ventricular stimulation pulse generators RV-STIM and LV-STIM, respectively. These trigger signals are generated each time that a stimulation pulse is to be generated by the respective pulse generator RA-STIM, RV-STIM or LV-STIM. The atrial trigger signal is referred to simply as the "A-pulse", and the ventricular trigger signal is referred to as the "V-pulse". During the time that either an atrial stimulation pulse or ventricular stimulation pulse is being delivered to the heart, the corresponding sensing stage, RA-SENS, RV-SENS and/or LV-SENS, is typically disabled by way of a blanking signal presented to these amplifiers from the control unit CTRL 54, respectively. This blanking action prevents the sensing stages RA-SENS, RV-SENS and LV-SENS from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

In order to successfully stimulate a heart chamber, a stimulation pulse needs to have strength above capture threshold of that heart chamber. Stimulation pulse strength can be altered by changing the amplitude and/or the pulse with of a stimulation pulse. Control unit CTRL 54 and stimulation pulse generators RA-STIM, RV-STIM and LV-STIM are adapted to adjust the pulse strength of stimulation pulses in order provide stimulation pulses that have a strength sufficient to cause capture without requiring excessive energy in order to avoid unnecessary depletion of the pacemaker's battery.

This is achieved by verification of capture on a beat-by-beat basis as disclosed hereinafter under "Automatic Capture Management" with respect to FIGS. 23 and 24.

Furthermore, atrial sense events As recorded shortly after delivery of a ventricular stimulation pulses during a preset time interval called post ventricular atrial refractory period (PVARP) are generally recorded as atrial refractory sense event Ars but ignored.

Control unit CTRL 54 comprises circuitry for timing ventricular and/or atrial stimulation pulses according to an adequate stimulation rate that can be adapted to a patient's hemodynamic need as pointed out below.

Basic timing intervals are, among others, an atrioventricular delay (AV-delay, AVD) between an atrial event and a scheduled right ventricular stimulation pulse and an interventricular delay (VV-delay, VVD) between a right (or left) ventricular event and the subsequently scheduled left (or right) ventricular stimulation pulse. These and other timing intervals such as atrial or ventricular escape intervals are controlled by control unit CTRL 54.

Still referring to FIG. 3, the implantable medical device 10 includes a memory circuit MEM 56 that is coupled to the control unit CTRL 54 over a suitable data/address bus ADR. This memory circuit MEM 56 allows certain control parameters, used by the control unit CTRL 54 in controlling the operation of the implantable medical device 10, to be stored and modified by the external programmer, as required, in order to customize the implantable medical device's operation to suit the needs of a particular patient. Such data includes the basic timing intervals used during operation of the pacemaker 10 and AV delay values and hysteresis AV delay values in particular.

Further, data sensed during the operation of the implantable medical device 10 may be stored in the memory MEM 56 for later retrieval and analysis.

A telemetry circuit TEL 58 is further included in the implantable medical device 10. This telemetry circuit TEL 58 is connected to the control unit CTRL 54 by way of a suitable command/data bus. Telemetry circuit TEL 58 allows for wireless data exchange between the implantable medical device 10 and an external device 80 or some remote programming or analyzing device which can be part of a centralized service center serving multiple pacemakers.

The implantable medical device 10 in FIG. 3 is referred to as a three chamber pace-maker/cardioverter/defibrillator because it interfaces with the right atrium 26, the right ventricle 28 and the left ventricle of the heart 12. Those portions of the pacemaker 10 that interface with the right atrium, e.g., the lead 14, the P-wave sensing stage A-SENSE, the atrial stimulation pulse generator A-STIM and corresponding portions of the control unit CTRL 54, are commonly referred to as the atrial channel. Similarly, those portions of the pacemaker 10 that interface with the right ventricle 28, e.g., the lead 16, the R-wave sensing stage V-SENSE, the ventricular stimulation pulse generator V-STIM, and corresponding portions of the control unit CTRL 54, are commonly referred to as the right ventricular channel.

In order to be able to detect periods of physical activity of a patient indicating that the patient is awake and in order to allow rate adaptive pacing in a DDDR or a DDIR mode, the pacemaker 10 further includes a physiological sensor ACT 60 that is connected to the control unit CTRL 54 of the pacemaker 10. While this sensor ACT 60 is illustrated in FIG. 2 as being included within the pacemaker 10, it is to be understood that the sensor may also be external to the implantable medical device 10, yet still be implanted within or carried by the patient. A common type of sensor is an accelerometer, such as a piezoelectric crystal, mounted to the case of the pacemaker. Other types of physiologic sensors are also known, such as sensors that sense the oxygen content of blood, respiration rate, blood pH, intracardiac impedance changes, and the like. The type of sensor used is not critical to the present invention. Any sensor capable of sensing some physiological parameter relatable to physical activity of a patient can be used. Such sensors are commonly used with "rate-responsive" pacemakers in order to adjust the rate of the pacemaker in a manner that tracks the physiological needs of the patient.

The control unit CTRL 54 is adapted to determine an adequate heart rate or stimulation rate in any manner known as such.

For impedance measurement, an impedance determination unit 70 is provided. Impedance determination unit 70 comprises a constant current source 72 that is connected or can be connected to electrodes for intracorporal placement as shown in FIG. 2. In order to allow for a plurality of impedance measurement electrode configurations, preferably some means of switching is provided between the constant current source 72 and the electrode terminals of the implantable medical device 10. The switch is not shown in FIG. 3. Rather, particular impedance measurement configurations are shown as examples.

Similarly, an impedance measuring unit 74 for measuring a voltage corresponding to a current fed through a body by the constant current source is provided and can be connected to a number of electrodes although a switch for switching between these configurations is not shown in FIG. 3.

As an alternative to constant current source 72, a constant voltage source can be provided. Then, the measuring unit will be adapted to measure a current strength of a current fed through a body by the constant voltage source.

Both constant current source 72 and impedance measurement unit 74 are connected to an impedance value determination unit 76 that is adapted to determine an impedance value for each measuring current pulse delivered by the constant current source 72.

The impedance value determination unit 76 comprises another analog to digital converter ADC in order to generate a digital impedance signal that is fed to the control unit CTRL 54.

Further, a pressure sensor PRESS 78 for sensing a pressure in the interior of housing 42 and a temperature sensor TEMP 79 for sensing a temperature in housing 42 are provided. Both sensors 78 and 79 are connected to control unit CTRL 54 via an analog to digital converter.

Control unit CTRL 54 further comprises watchdog and reset units to provide safety when the CPU should fail. The watchdog units therefore are designed to operate independently from the CPU of the control unit CTRL 54. In FIG. 3, the watchdog and reset units are not shown.

Signal Template

As discussed above, most biological signals show distinctive patterns. A common practice to characterize a distinctive signal pattern is to construct a signal template based on representative signals.

In one embodiment, the biological signal template is static, that is, it can be predefined according to well-known knowledge of the biological signal, and programmed into the IPG memory. In another embodiment, the biological signal template is automatically constructed from the measured biological signals under well-control conditions.

Figure 4:
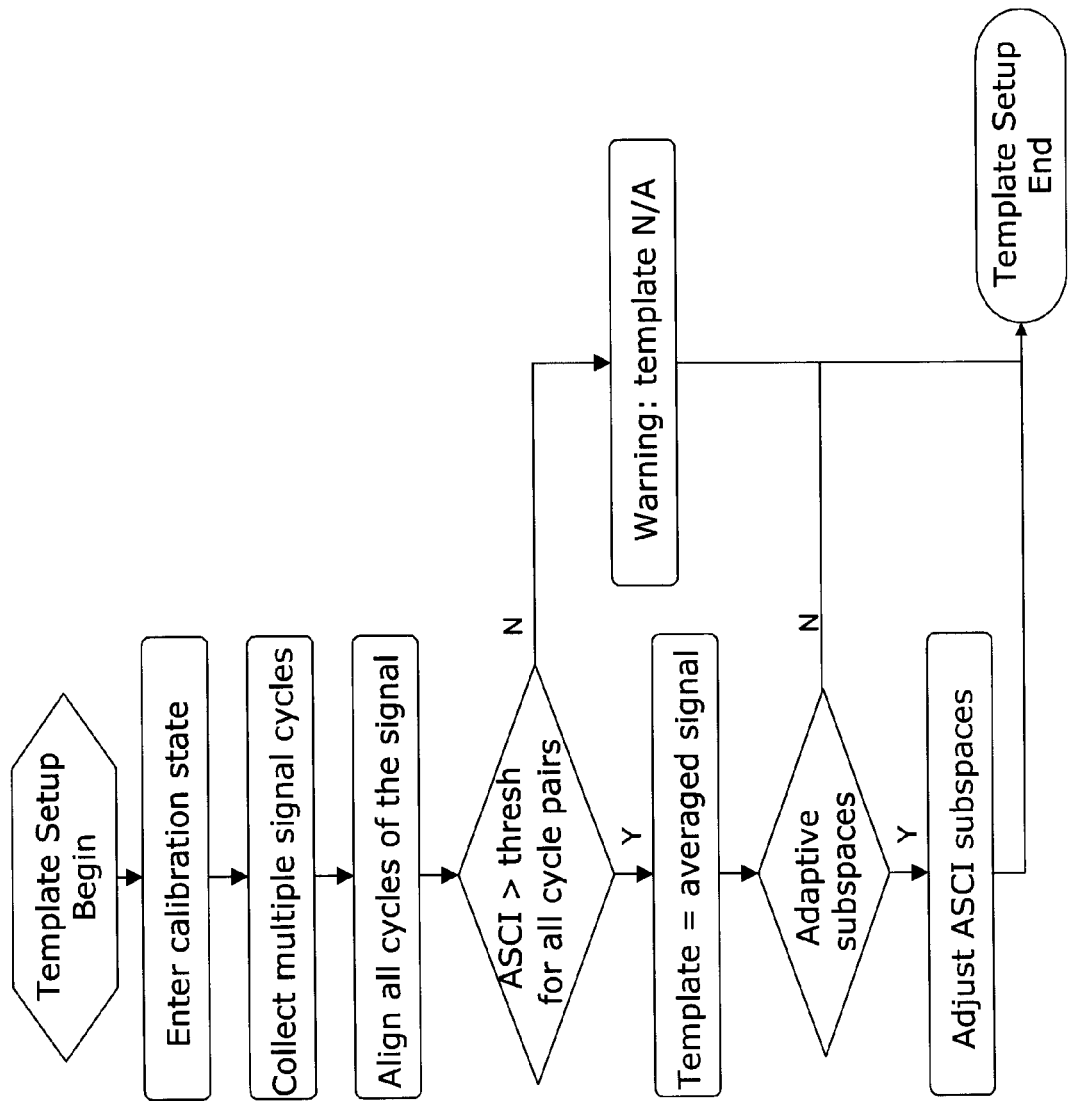
FIG. 4 shows a high-level flowchart diagram that illustrates the steps involved in automatic setup of the biological signal template.

FIG. 4 shows a high-level flowchart diagram that illustrates the steps involved in automatic setup of the biological signal template in an IPG. First, the IPG enters a specific calibration state that is believed to maximize the possibility of recording the desired biological signal with a stable pattern. Then the IPG collects multiple cycles of the desired biological signal, which is usually properly filtered and amplified to achieve satisfactory signal to noise ratio. The collected multiple cycles of the biological signals are then aligned based on particular event trigger, or based on predefined fiducial point, for example, the positive or negative or absolute peak, the maximum slope, the threshold crossing (including zero-crossing) point, etc., as known in the art. According to this invention, for each pair of the aligned biological signals, their morphological similarity is quantified by an Adaptive Signed Correlation Index, or ASCI. If for any given cycle pair, the calculated ASCI is lower than a predefined threshold value, then the collected biological signal cycles are considered not stable. A warning is generated by the IPG indicating the template signal is not available at the moment, and the template setup may be retried at a later time. On the other hand, if for all cycle pairs, the calculated ASCI is greater than the predefined threshold value, then all collected signal cycles are considered similar, and the biological signal template is created by averaging all these aligned signal cycles. As discussed in more details later, the ASCI is calculated based on definition of three subspaces. If the adaptive subspace feature is enabled, the IPG further adjust the three subspaces as discussed thereinafter.

With respect to an implantable heart stimulator the morphology of the captured IEGM waveform not only depends on the pace chamber, but also is affected by the pace electrode configuration (bipolar, unipolar, extended bipolar, etc.) and the sense electrode configuration (tip-ring, tip-can, coil-can, etc.). Therefore, according to this invention, a specific template waveform representing captured pace is generated for each pace and sense configuration of the corresponding heart chamber. That is, for continuous capture classification of specific heart chamber (RA, RV, LV), proper template waveform shall be used with compatible pace and sense configuration for that specific heart chamber.

Note that for capture classification, although the unipolar sense configuration (with widely spaced electrodes) is preferred over the bipolar sense configuration (with closely spaced electrodes) because the former senses electrical activity from a larger volume of the myocardium, the present invention is applicable to all sense configurations as long as the captured waveform morphology is different than that of the non-captured pace.

Figure 5:
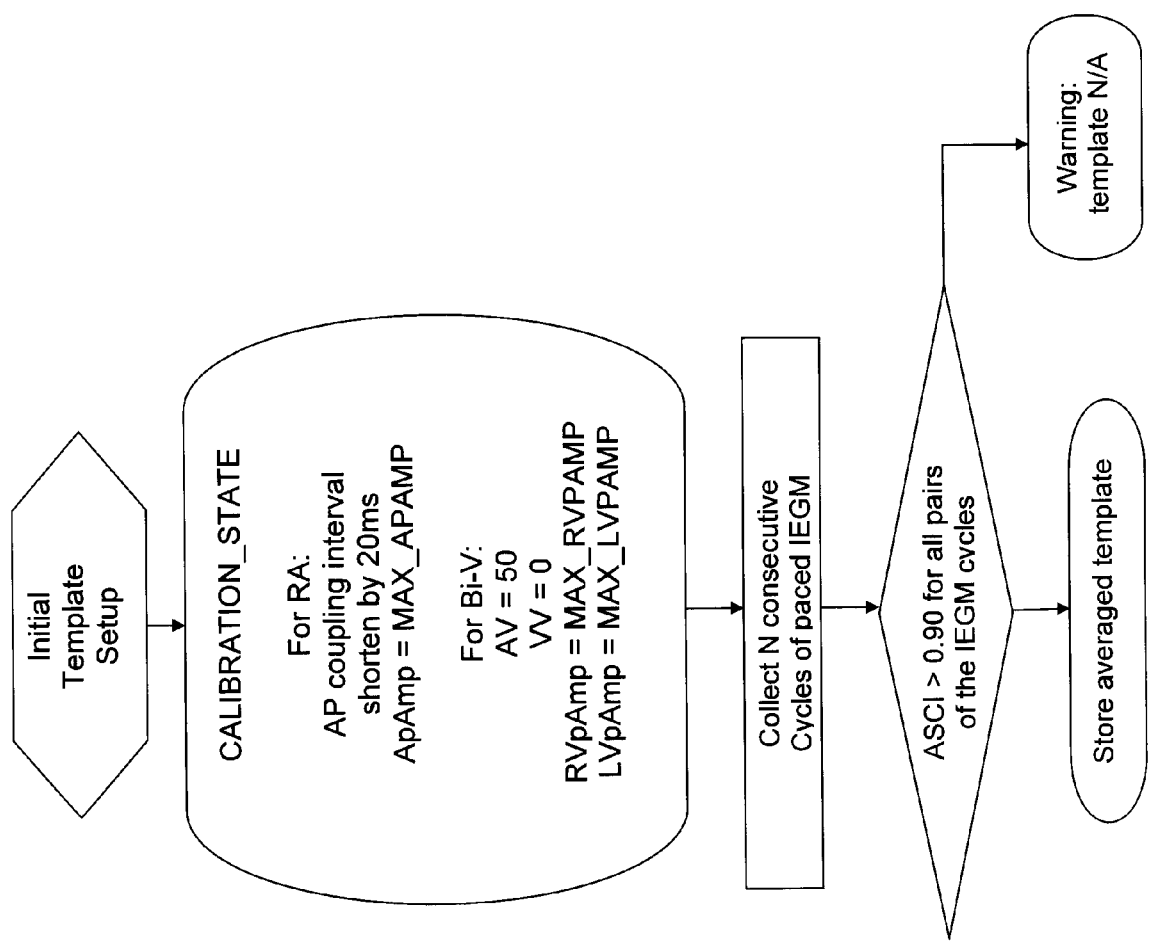
FIG. 5 illustrates the initial setup phase of creating the template waveform.

Refer to FIG. 5. For each pace/sense configuration of specific heart chamber, the corresponding template waveform is created through the initial setup phase. In one embodiment, the initial setup phase starts automatically, for example, after initial implant or follow-up, after pace/sense configuration change, or periodically at scheduled time (e.g., midnight), etc. In another embodiment, the initial setup phase can be triggered manually by programming the device through an external programmer.

Still refer to FIG. 5. For initial template setup, the device enters the calibration state with controlled parameters settings. In a preferred embodiment, for the RA chamber, the AP coupling interval (or atrial escape interval) is temporarily shortened (e.g., 20 ms less than the average atrial cycle length measured over multiple sensed/paced beats prior to the setup phase) to ensure atrial overdrive pacing. The AP amplitude is programmed to the predefined max amplitude (MAX_APAMP) that is considered sufficient for atrial capture. For the RV and LV chambers, overdrive bi-ventricular pacing is ensured (and the likelihood of ventricular fusion is minimized) by temporarily shortening the device AV delay (AVD), preferable to 50 ms, and temporarily setting the device VV delay (VVD) to 0 ms. In addition, the RV and LV pace amplitudes are respectively programmed to their predefined max amplitudes, MAX_RVPAMP and MAX_LVPAMP, that are considered sufficient for RV and LV captures.

Still refer to FIG. 5. After setting the parameters in the calibration state, the device collects N (preferably 8) consecutive cycles of paced IEGM of the corresponding chamber. Presumably all N beats are captured due to overdrive pacing with programmed max pacing amplitude. Then the similarity between each possible pair of the N cycles is quantified by the Adaptive Signed Correlation Index (ASCI), which will be described in more detail below. For N cycles, there are total $N(N+1)/2$ cycle pairs for calculation of the ASCI. If for any given pair the calculated ASCI is below a predefined/user-programmable threshold (preferably 0.90), then it indicates that the pair has different waveform morphology. Consequently, a warning is generated to indicate that the template waveform is currently not available, and the initial template setup can be restarted later. On the other hand, if the calculated ASCI for all $N(N+1)/2$ pairs are greater than the predefined/user-programmable threshold, then it indicates that all N cycles have consistent waveform morphology. Consequently, the N cycles IEGM are averaged to generate the template waveform.

For generating the template waveform, all paced cycles are aligned based on the respective pacing pulse (indicated by the device-generated pacemarker), and then averaged point-by-point for the full length of the template waveform. In a preferred embodiment, the template waveform starts from the first sample point after pacing pulse (indicated by the device-generated pacemarker), and the template waveform spans from the evoked potential to the repolarization phase of the IEGM. In an exemplarily embodiment, the RA template waveform spans about 100 ms starting from the AP pulse, the RV template waveform spans about 350 ms from the RVP pulse, and the LV template waveform spans about 350 ms from the LVP pulse. Note that a short window (typically around 20 ms) immediately following the pacing pulse contains no meaningful waveform information due to programmed post-pace blanking to exclude the pacing artifact.

Figure 6:
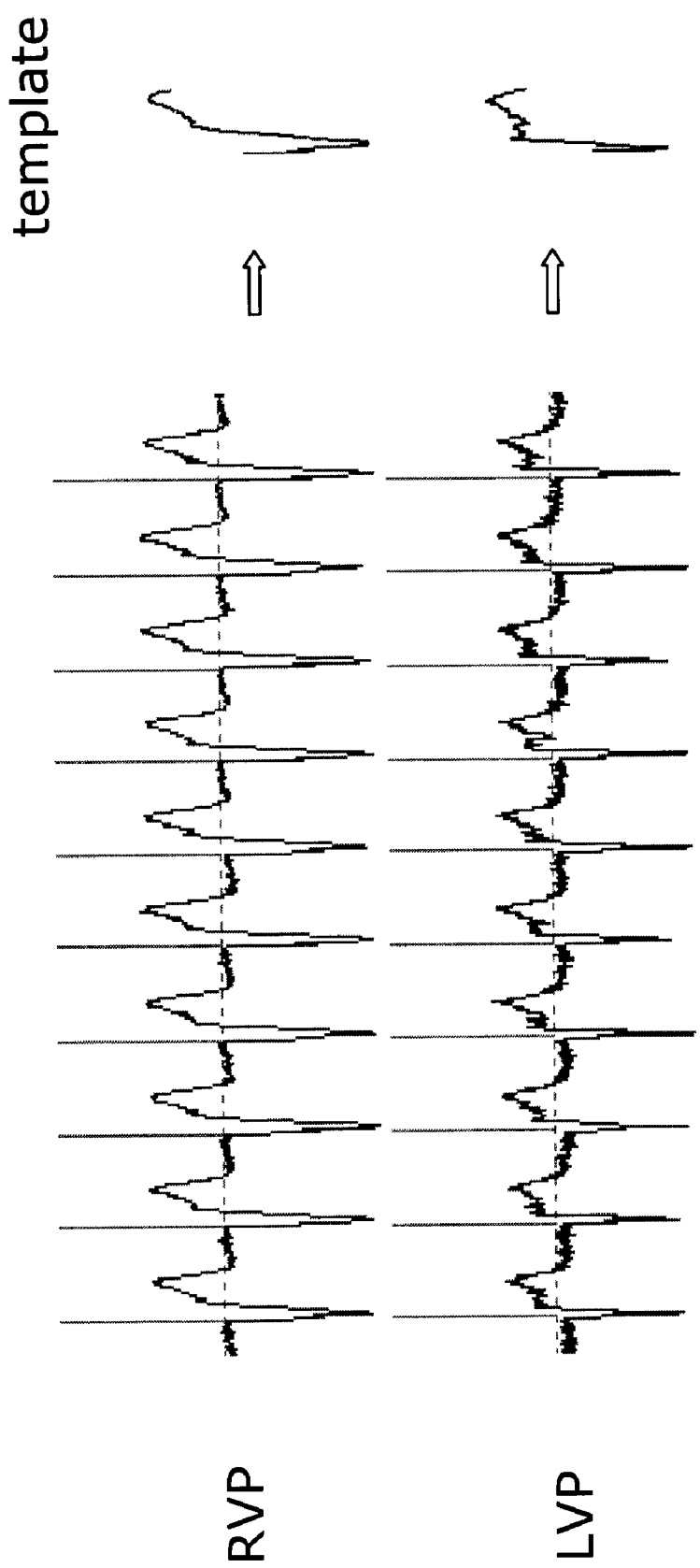
FIG. 6 is an example illustrating the generation of template waveforms by averaging multiple beats of captured paces.

Refer to FIG. 6. In this example, RV and LV are respectively captured by RVP and LVP (bipolar pacing and bipolar sensing for both chambers), with programmed VVD of 0 ms. Ten consecutive RVP cycles that have consistent waveform morphology are averaged to generate the RVP template waveform (bipolar pacing, bipolar sensing). Similarly, ten cycles of LVP cycles that have consistent waveform morphology are averaged to generate the LVP template waveform (bipolar pacing, bipolar sensing). Both template waveforms span 350 ms from the respective pacing pulse, thus covering part of the evoked potential phase (negative spike) and part of the repolarization phase (T wave).

In one embodiment, after the initial template setup, the template is fixed until the next template setup phase. In another embodiment, the device can be programmed to enable template running update, that is, the template waveform can be continuously updated on a beat-by-beat basis. By this means, the template waveform can be dynamically adjusted to reflect possibly chronic change of the captured waveform morphology due to many factors, such as medication, circadian variation, disease progression, and so on.

According to a preferred embodiment of this invention, after the initial template setup, the biological signal template is preferably updated continuously during normal operation of the IPG.

Figure 7:
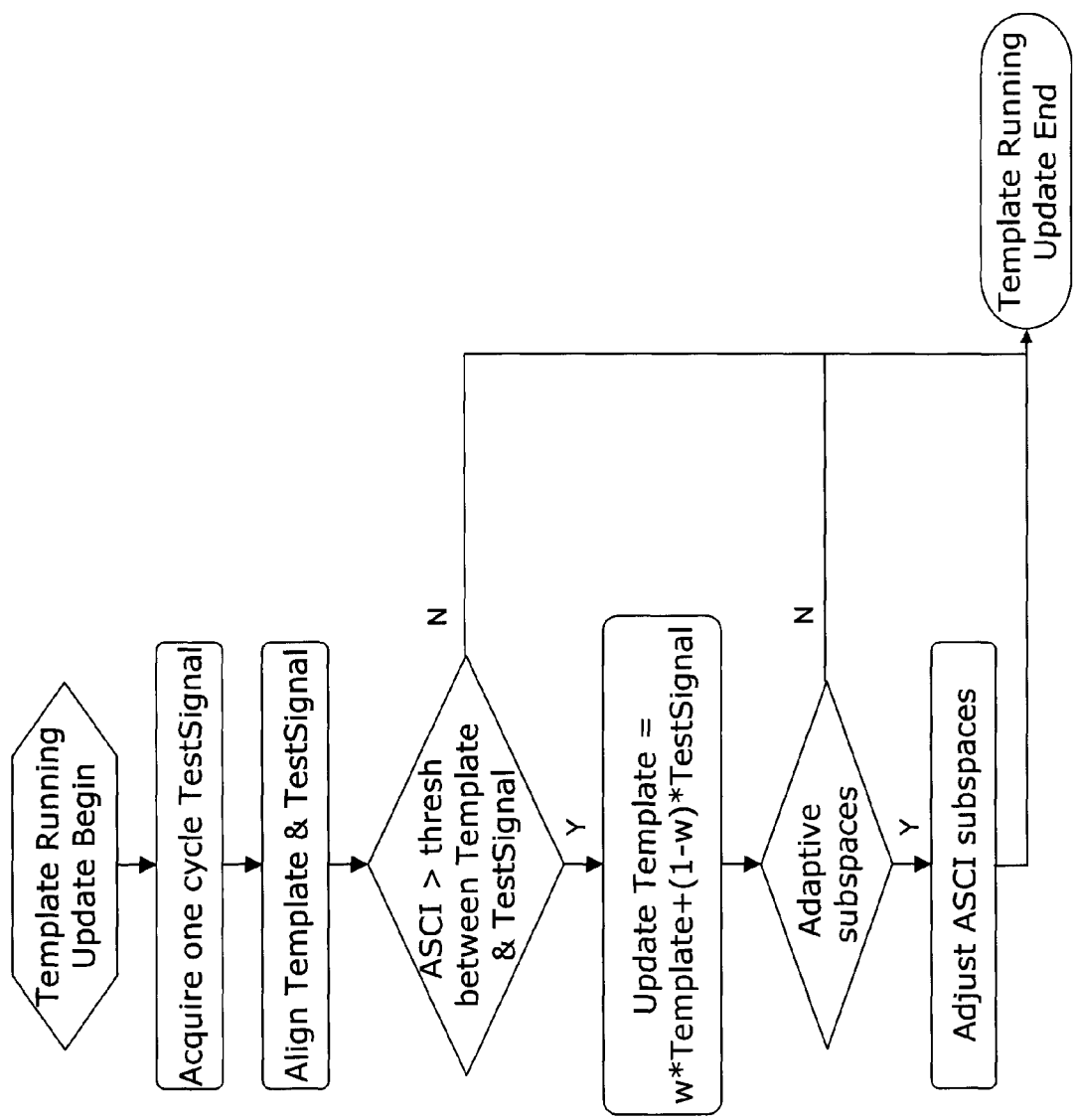
FIG. 7 shows a high-level flowchart diagram that illustrates the steps involved in the running update of the biological signal template.

FIG. 7 shows a high-level flowchart diagram that illustrates the steps involved in running update of the biological signal template. During normal operation, the IPG acquires one cycle of test signal, and aligns the test signal with the template signal based on predefined fiducial point as discussed above with respect to FIG. 4. Then the IPG calculates the ASCI between the template signal and the acquired test signal. If the ASCI is lower than a predefined threshold value, then the test signal is considered different than the template signal, and no template update is performed for this test cycle. On the other hand, if the calculated ASCI is greater than the predefined threshold, then the test signal is considered similar to the template signal, and the template signal is updated by taking the weighted average of the original template signal and the newly acquired test signal. In an exemplary embodiment, the new template is the sum of the old template signal scaled by 255/256, and the newly acquired test signal scaled by 1/256. By this means, it ensures the stability of the template waveform by retaining 255/256 of the old template signal, whereas it incorporates 1/256 of the test signal to factor in any gradual change of the signal pattern. Similarly, if the adaptive subspace feature is enabled, the IPG further adjust the three subspaces as discussed thereinafter.

Figure 8:
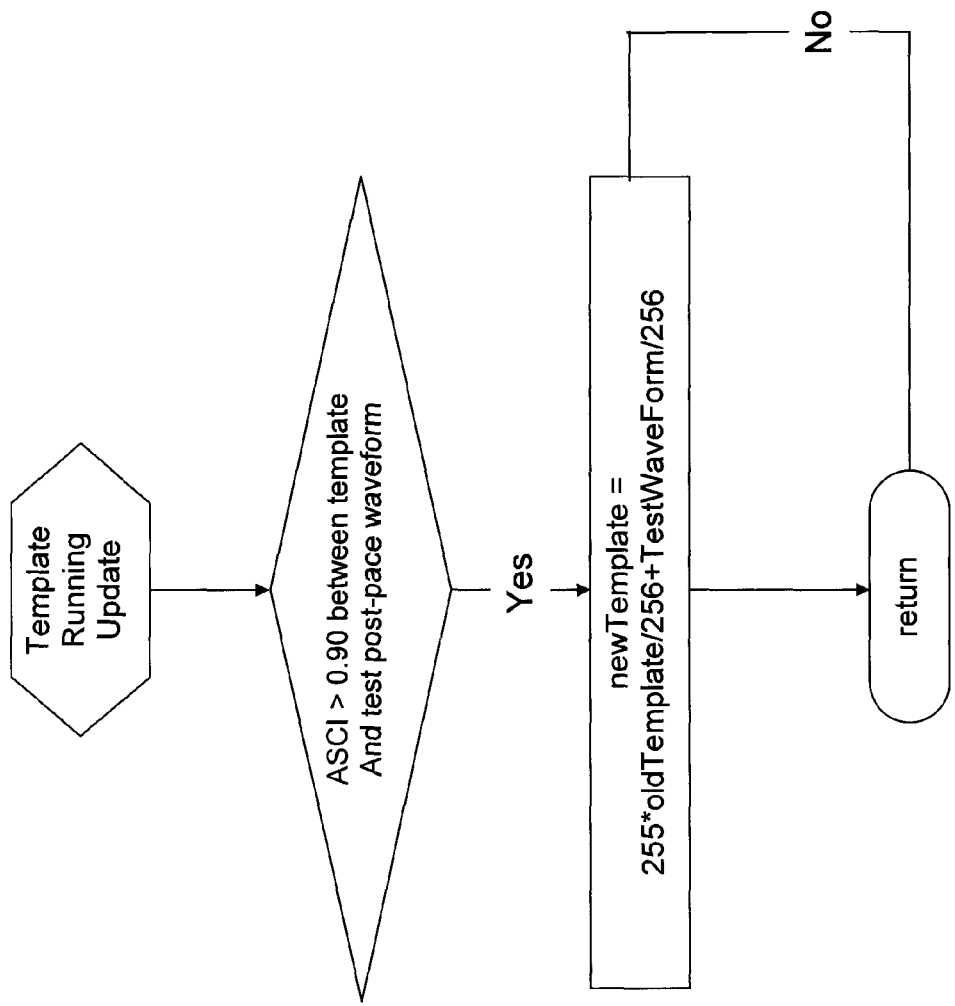
FIG. 8 illustrates the running update of the template waveform.

Now refer to FIG. 8 showing a specific flowchart illustrating a template update for a capture template. When template running update feature is enabled, the device continuously monitors each pace, and evaluates its capture status by calculating the ASCI between the pair of template waveform and the incoming test waveform. If the post-pace waveform morphology is consistent with the template waveform, evidenced by ASCI being greater than a predefined/user-programmable threshold (preferably 0.90), then the pace status is confirmed as capture, and the template waveform is updated by means of weighted average of the old template waveform and the new test waveform.

Figure 9:
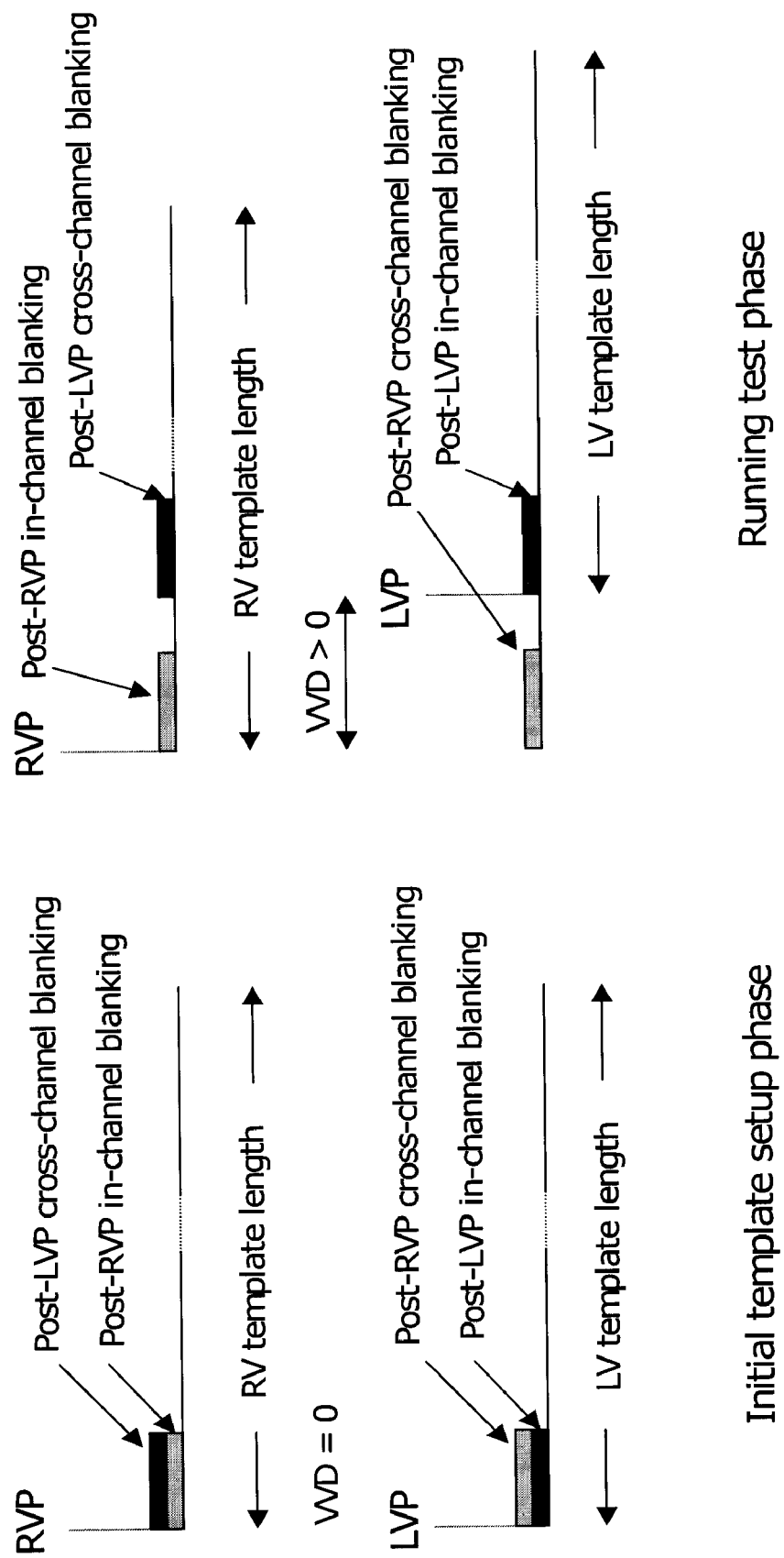
FIG. 9 is a schematic illustration of different post-pace blanking windows during initial template setup phase and the running test phase.

Refer to FIG. 9. It is understood that the post-pace blanking window used for initial template setup could differ from the one used for the test waveform. For example, the VVD is set to 0 ms during initial template setup phase, but it could be non-zero (positive or negative) during the running test phase. Each RVP starts an in-channel blanking window in the RV chamber as well as a cross-channel blanking window in the LV chamber. Similarly, each LVP starts an in-channel blanking window in the LV chamber as well as a cross-channel blanking window in the RV chamber. Consequently, both the timing and length of the effective RV or LV blanking window in the running test phase could be different than those in the initial template setup phase.

According to this invention, when template running update feature is enabled, only the un-blanking portion of the test waveform is used to update the corresponding portion of the template waveform. In other words, the segment(s) of template waveform that correspond to the blanking window of the test pace is kept unchanged, whereas the segment(s) of template waveform that correspond to the un-blanked test waveform are updated by means of the weighted average method. Mathematically, denote TEMP as the vector of the template waveform with L samples, and TEST as the vector of the test waveform with the same length L. Then the running update can be formulated as:

$$TEMP(i) = \begin{cases} TEMP(i) & i \in \text{blanking window of test pace} \\ 255 \cdot TEMP(i)/256 + TEST(i)/256 & i \notin \text{blanking window of test pace} \end{cases}$$

Here, TEMP(i) is the $i^{th}$ sample amplitude of the template waveform, and TEST(i) is the $i^{th}$ sample amplitude of the test waveform, where $0 < i \leq L$.

Signal Trichotomization

Before calculating the ASCI between two biological signals, both signals (template waveform and the test waveform) are trichotomized. The concept of signal trichotomization is described in this section.

Let R denotes the signal space, which is divided into three subspaces $R_P$, $R_Z$, and $R_N$ such that $R = R_P \cup R_Z \cup R_N$ and $R_P \cap R_Z = R_P \cap R_N = R_Z \cap R_N = \emptyset$, where $\cup$ is the union operator, $\cap$ is the intersection operator, and $\emptyset$ represents the null space. That is, the three subspaces are non-overlapping yet all together they span the whole signal space.

Further denote S as the three-value set $\{-1, 0, 1\}$. Assume $X = [x(1), x(2), \ldots, x(L)]$ is a signal in R, that is, $x(i) \in R$ for $i = 1, 2, \ldots L$, where L is the number of samples in signal X. Mathematically, denote $X = [x(1), x(2), \ldots, x(L)]$ as the vector of a template or test waveform with L samples, and denote $TX = [tx(1), tx(2), \ldots, tx(L)]$ as its trichotomized vector of the same length. Trichotomization of signal X is an operation that maps the signal from R space to S space. Specifically, denote $TX = [tx(1), tx(2), \ldots, tx(L)]$ as the trichotomized signal of X, where $tx(i) \in S$ for $i = 1, 2, \ldots L$. Then the trichotomization is formulated as, for $$tx(i) = \begin{cases} 1 & \text{if } x(i) \in R_P \\ 0 & \text{if } x(i) \in R_Z \\ -1 & \text{if } x(i) \in R_N \end{cases}$$

In other words, signal X is trichotomized to TX by converting all its data samples to values selected from the set $\{-1, 0, 1\}$, according to which subspace each data sample belongs to.

Adaptive Subspaces

It is understood that the signal space R and its subspaces $R_P$, $R_Z$, and $R_N$ can be one-dimensional, two-dimensional, or multi-dimensional. For convenient purpose, in the following descriptions, we term $R_P$ as the positive subspace, $R_Z$ as the zero subspace (or baseline subspace), and $R_N$ as the negative subspace.

According to this invention, both positive subspace ($R_P$) and the zero subspace ($R_Z$) are adaptive to a template signal in R, consequently the negative subspace ($R_N$) is also adaptive to the template signal. In a typical embodiment, signal X is the template signal, and ASCI(X,Y) measures the similarity between signal Y and the template signal X.

Accordingly, the subspaces $R_P$, $R_Z$, and $R_N$ are adaptive to the template signal X. For illustration purpose, the following descriptions are based on the assumption that X is the template signal, although it should be understood that ASCI(X,Y) can be calculated based on a different template signal while the same principles apply.

According to specific need of the application and/or prior knowledge of the biological signal, there are many different means to define the subspaces $R_P$, $R_Z$, and $R_N$ based on the template signal. For illustration purpose, X and Y are represented as two one-dimensional signals in the following examples.

Figure 10:
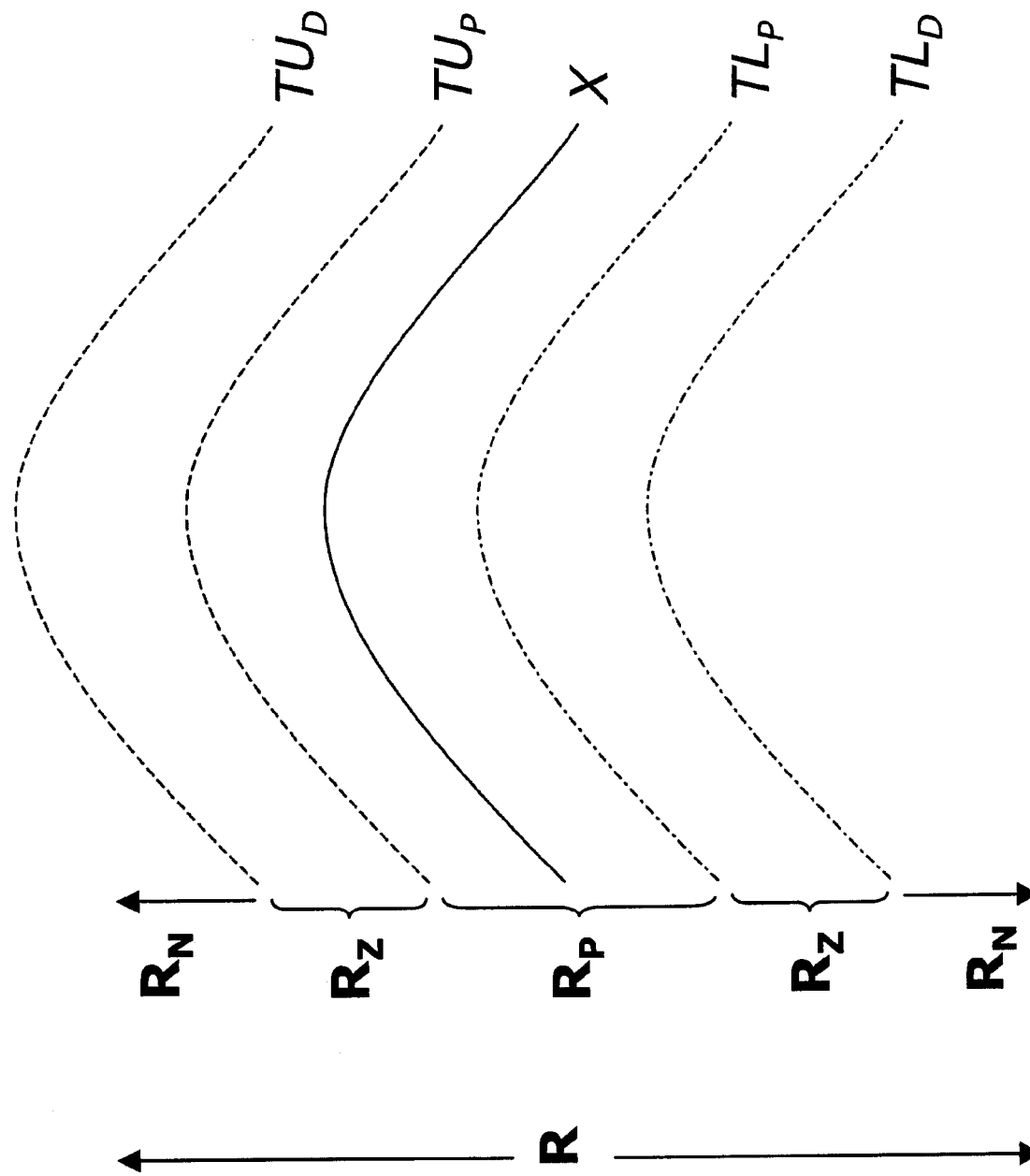
FIG. 10 shows an example of defining threshold vectors from a template signal X.

Refer to FIG. 10. In a preferred embodiment, four threshold vectors TLD, TLP, TUP, TUD are defined from the template signal X. Denote $TLP = [tlp(1), tlp(2), \ldots, tlp(L)]$ as the proximal lower threshold vector, $TLD = [tld(1), tld(2), \ldots, tld(L)]$ as the distal lower threshold vector, $TUP = [tup(1), tup(2), \ldots, tup(L)]$ as the proximal upper threshold vector, and $TUD = [tud(1), tud(2), \ldots, tud(L)]$ as the distal upper threshold vector. These threshold vectors are defined such that $TLD \leq TLP \leq X \leq TUP \leq TUD$, or specifically, $tld(i) \leq tlp(i) \leq x(i) \leq tup(i) \leq tud(i)$, for $1 \leq i \leq L$. The positive subspace $R_P$ is defined as the region bounded by TLP and TUP, the negative subspace $R_N$ is defined as the region above TUD or below TLD, and the zero subspace $R_Z$ is defined as the region bounded between TUP and TUD, and that between TLD and TLP. Obviously, a sample in $R_P$ is proximal to the template, a sample in $R_N$ is distal to the template, and a sample in $R_Z$ is at intermediate distance to the template. For the template signal X, all elements of its trichotomized signal TX are 1 because all samples of X are within the positive subspace $R_P$. For another signal Y, its trichotomized signal TY will have more 1s if more samples of Y are close to the corresponding samples of X, i.e., Y is similar to X. As Y gradually deviates from X, its trichotomized signal TY has less 1s, more 0s, and eventually more −1s.

Figure 11:
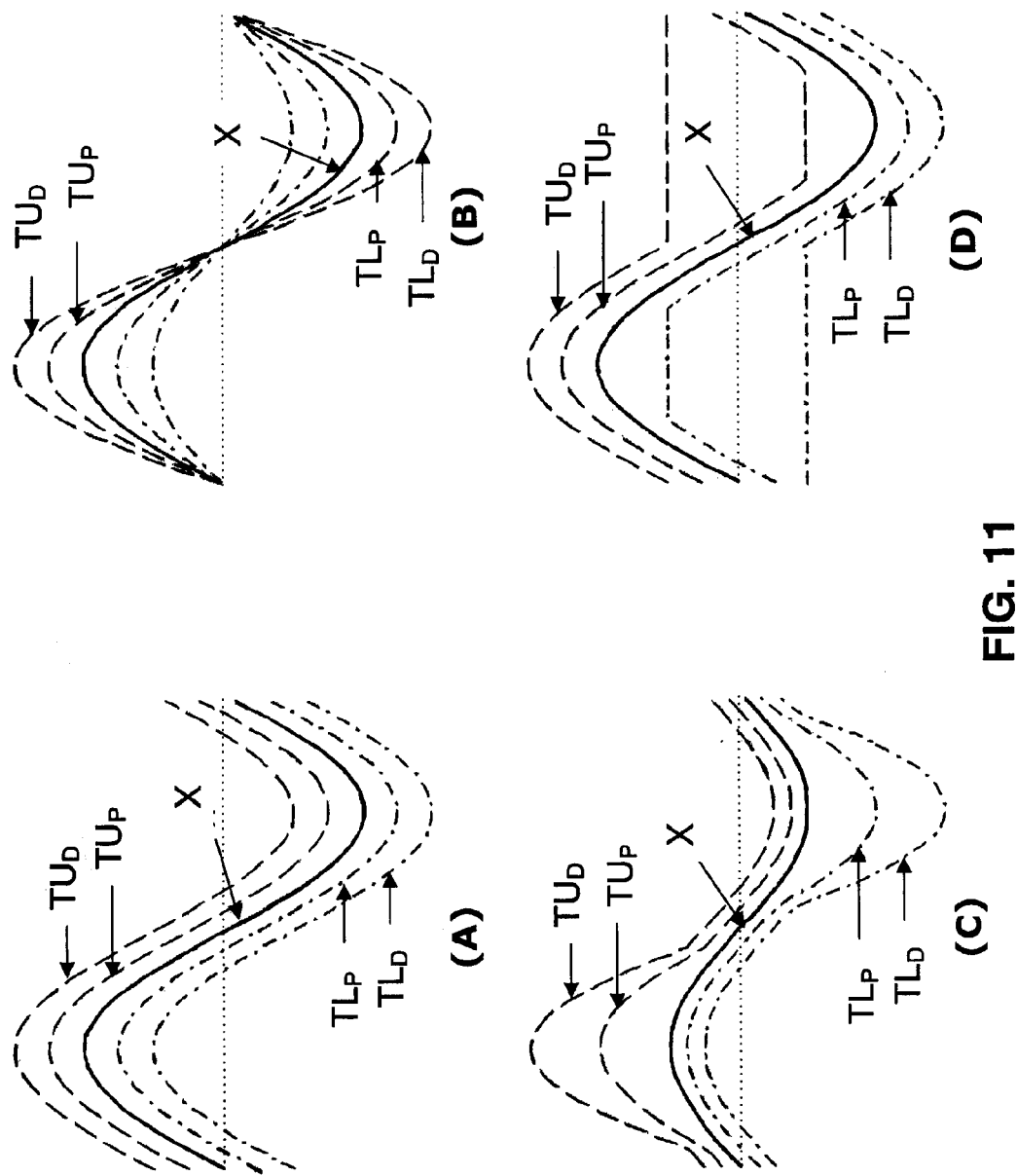
FIG. 11 shows four further examples of defining threshold vectors from the template signal X.

For illustration purpose, FIG. 11 shows four examples of defining threshold vectors from the template signal X. In each example, the four threshold vectors are either defined based on sample-by-sample amplitude of X, or based on the max absolute amplitude of X, or based on both. The resulting threshold vectors can be symmetrical or asymmetrical around the signal X. Obviously, there are numerous other means to define the four threshold vectors so that they are adaptive to the template signal X, for example, either based on sample-by-sample amplitude of X, or based on specific features of X, such as its maximum, minimum, max absolute, mean, median, etc., or their combinations.

Figure 12:
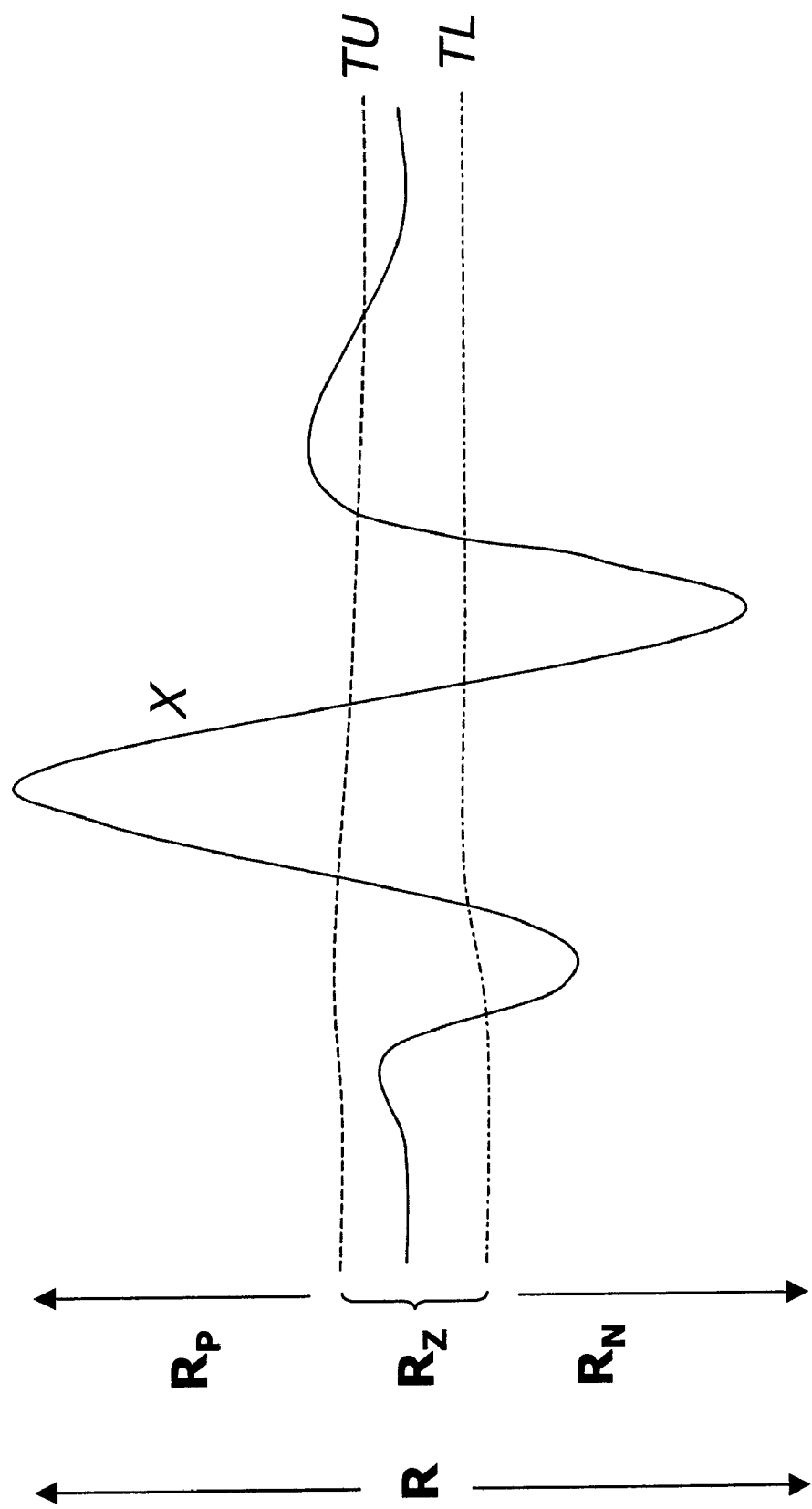
FIG. 12 shows another example where two threshold vectors TL and TU are defined from the template signal X.

Refer to FIG. 12. In another typical embodiment, two threshold vectors TL and TU are defined from the template signal X. Denote $TL = [tl(1), tl(2), \ldots, tl(L)]$ as the lower threshold vector, $TU = [tu(1), tu(2), \ldots, tu(L)]$ as the upper threshold vector, and they are defined such that $TL \leq TU$, or specifically, $tl(i) \leq tu(i)$, for $1 \leq i \leq L$. The positive subspace $R_P$ is defined as the region above TU, the negative subspace $R_N$ is defined as the region below TL, and the zero subspace $R_Z$ is defined as the region bounded between TL and TU. Intuitively, a sample in $R_P$ indicates more positive amplitude, a sample in $R_N$ indicates more negative amplitude, and a sample in $R_Z$ indicates intermediate amplitude. For the template signal X, the elements of its trichotomized signal TX can be 1, 0, or −1, depending on the relative sample amplitude of X with respect to the threshold vectors.

Then the trichotomization can be formulated as, for $0 < i \leq L$, $$tx(i) = \begin{cases} 1 & x(i) > tu(i) \\ 0 & tl(i) \leq x(i) \leq tu(i) \\ -1 & x(i) < tl(i) \end{cases}$$

Adaptive Threshold and Vector Trichotomization

Figure 13:
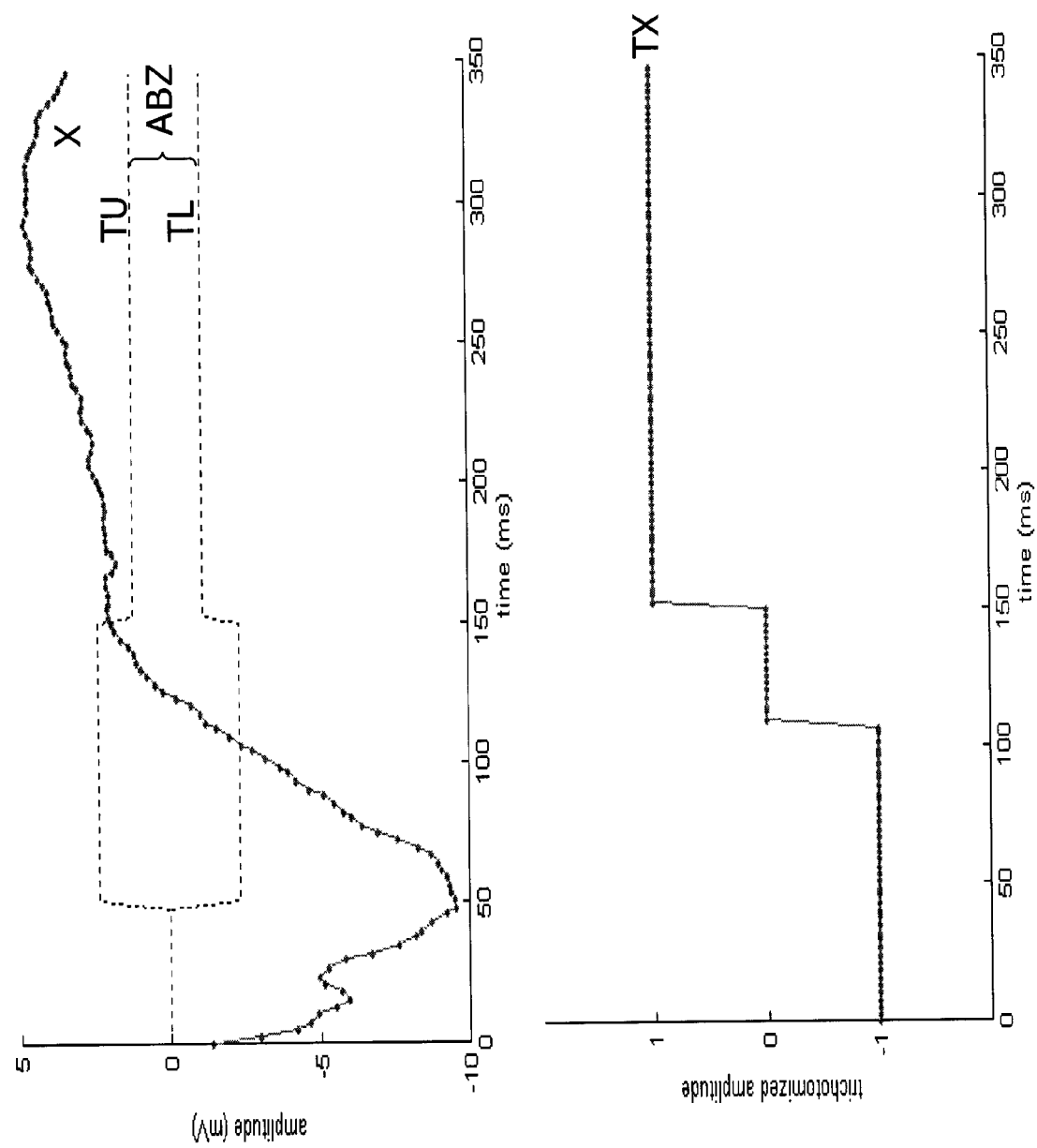
FIG. 13 illustrates the concept of waveform trichotomization based on adaptive threshold.

Refer to FIG. 13. The vectors TU and TL collectively define the Adaptive Baseline Zone (ABZ). For a given waveform, any sample whose amplitude falls into the ABZ is treated as 0 after trichotomization. On the other hand, any sample whose amplitude is above the ABZ is treated as +1 after trichotomization, whereas any sample whose amplitude is below the ABZ is treated as −1 after trichotomization. Therefore, the trichotomized vector TX is an approximate representation of the original waveform X with varying quantization resolution. Importantly, the trichotomized waveform faithfully preserves the phase information of each sample (+1 for positive sample, −1 for negative sample, 0 for sample near the baseline) of the original waveform.

According to this invention, both the positive threshold vector TU and the negative threshold vector TL are time-variant and adaptive to the peak amplitude of the template waveform (MAX_TEMP). For RVP or LVP, MAX_TEMP usually corresponds to the max amplitude of the T wave included in the template waveform. In a preferred embodiment, TU and TL are symmetrical around the baseline (i.e., TU=−TL), and are defined by the following formula:

$$tu(i) = -tl(i) = \begin{cases} 0 & 1 \leq i < L1 \\ \text{MAX\_TEMP}/2 & L1 \leq i < L2 \\ \text{MAX\_TEMP}/4 & L2 \leq i \leq L \end{cases}$$

Here, L is the length of the waveform, and $0 < i \leq L$. Note that TU and TL have three segments. For the first segment ($1 \leq i < L1$), both TU and TL are set to zero. For the second segment ($L1 \leq i < L2$), TU (=−TL) is set to one half of MAX_TEMP. For the third segment ($L2 \leq i \leq L$), TU (=−TL) is set to one quarter of MAX_TEMP.

In a typical embodiment, for RVP and LVP, the waveform length L corresponds to 350 ms. Accordingly, the first segment ($1 \leq i < L1$) corresponds to 0-50 ms, the second segment ($L1 \leq i < L2$) corresponds to 50-150 ms, and the third segment ($L2 \leq i \leq L$) corresponds to 150-350 ms. For RAP, the waveform length L corresponds to 100 ms. Accordingly, the first segment ($1 \leq i < L1$) corresponds to 0-50 ms, the second segment ($L1 \leq i < L2$) corresponds to 50-70 ms, and the third segment ($L2 \leq i \leq L$) corresponds to 70-100 ms. Alternatively, the length of each segment can be user-programmable.

It is believed that the usage of adaptive threshold zone (ABZ) is advantageous than fixed threshold for characterizing the phase dynamics of a waveform. Conventionally, a waveform can be coded by comparing it with the baseline (fixed zero threshold). That is, a sample has positive phase if it is greater than zero, or has negative phase if it is less than zero. However, it is known that a waveform (particularly the IEGM waveform) can have many near-zero values due to limited input sampling resolution and the intrinsic baseline wandering of the signal. Therefore, a non-zero ABZ is preferred to characterize these near-baseline samples that lack apparent polarity.

Furthermore, the varying threshold of the ABZ described above is uniquely advantageous to characterize the phase dynamics of the evoked response after pacing. For example, a captured pace is expected to be followed by a downward spike. The first segment (e.g., 0-50 ms) of the ABZ has zero threshold, indicating all samples in this segment must be negative for a captured pace (i.e., no tolerance for positive or zero). The second segment (e.g., 50-100 ms for RVP and LVP) of the ABZ has wider thresholds, indicating more tolerance of the sample variation around the baseline. Such design is based on the observation that a captured waveform usually has zero-crossing in this segment, and wider ABZ allows more beat-to-beat variation of the zero-crossing point, for example, due to the intrinsic heart rate dependency of the QT intervals. The following segment (e.g., 100-350 ms for RVP and LVP) of the ABZ has narrower (but non-zero) thresholds. This allows robust coding of the sample phase (+1 or −1), meanwhile, being less sensitive to those near-baseline values (0).

In another embodiment, other segmentation methods can be used to define TU and TL. For example, TU and TL can have only one segment (i.e., fixed threshold for the full waveform length), or two segments (initial zero threshold, followed by fixed threshold), or four segments (initial zero threshold, followed by thresholds of ±MAX_TEMP/2, ±MAX_TEMP/4, and ±MAX_TEMP/8), and so on. Other segmental threshold values, such as MAX_TEMP/3, MAX_TEMP/5, etc., can also be used. Moreover, TU and TL may be asymmetric, and can be defined independently based on positive peak amplitude and negative peak amplitude of the template waveform, respectively.

In a further embodiment, TU and TL can be defined point-by-point (see e.g. FIG. 12) rather than segment-by-segment. Specifically, for the $i^{th}$ template sample x(i), where $0 < i \leq L$, the corresponding tp(i) and tn(i) can further adapt to the corresponding sample amplitude x(i). For example, it can be defined that:

If |x(i)| ≤ MAX_TEMP/4, THEN tu(i) = −tl(i) = MAX_TEMP/4;
ELSE IF x(i) > MAX_TEMP/4, THEN tu(i) = max(MAX_TEMP/4, x(i)/2) and tl(i) = 0;
ELSE [that is, x(i) < −MAX_TEMP/4], tu(i) = 0 and tl(i) = min(−MAX_TEMP/4, x(i)/2).

Figure 14:
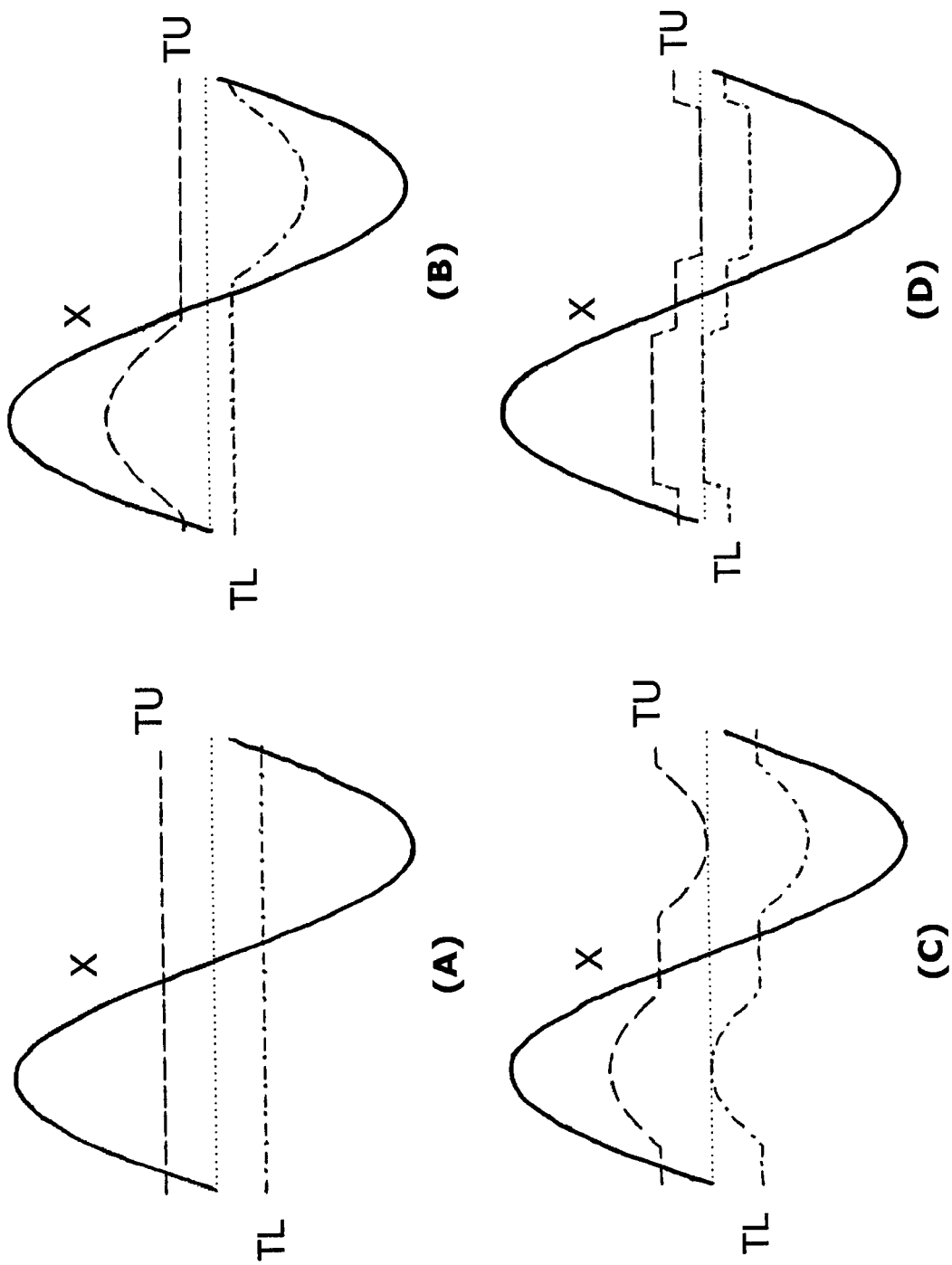
FIG. 14 shows four examples of defining threshold vectors from a template signal X.

For illustration purposes, FIG. 14 shows four examples of defining threshold vectors from the template signal X. In each example, the two threshold vectors are either defined based on sample-by-sample amplitude of X, or based on the max absolute amplitude of X, or based on both. The resulting threshold vectors can be symmetrical or asymmetrical around the baseline. Obviously, there are numerous other means to define the two threshold vectors so that they are adaptive to the template signal X, for example, either based on sample-by-sample amplitude of X, or based on specific features of X, such as its maximum, minimum, max absolute, mean, median, etc., or their combinations.

According to a preferred embodiment of this invention, when adaptive subspace feature is enabled for an IPG, the threshold vectors that define the three subspaces are further adjusted based on acquired signals. For example, during the initial template setup phase as illustrated in FIG. 4, after the template signal is constructed by averaging all aligned signal cycles, the three subspaces can be adjusted by redefining the threshold vectors. Specifically, for each sample of the template signal, which is obtained by calculating the average of N acquired samples from N aligned signal cycles, its corresponding upper and lower thresholds can be adjusted to further adapt to the statistics of these N acquired samples, for example, the difference between the maximum and minimum of the N acquired samples, the standard deviation of the N acquired samples, etc.

Similarly, during the template running update as illustrated in FIG. 7, after the template signal is updated by taking the weighted average of the old template signal and the new test signal, the three subspaces can be adjusted by redefining the threshold vectors. Specifically, for each sample of the template signal, which is calculated by taking the weighted average of the old template sample and the new test sample (aligned), its corresponding upper and lower thresholds can be adjusted to further take into account the new test sample.

Although the template signal and the threshold vectors shown in FIGS. 10 to 14 are represented as one-dimensional signals for illustration purpose, it should be understood the same concept is applicable to multi-dimensional signals (e.g., N-dimensional threshold surfaces can be constructed from the N-dimensional template signal to divide the N-dimensional signal space into $R_P$, $R_Z$, and $R_N$ subspaces).

Adaptive Signed Correlation Index

Now the method for calculating Adaptive Signed Correlation Index (ASCI) is described below in detail.

Denote $X=[x(1), x(2), \ldots, x(L)]$ and $Y=[y(1), y(2), \ldots, Y(L)]$ are two waveform vectors (signal vectors), each of which has L samples. Applying the adaptive threshold vectors TU and TL as described above with respect to FIG. 13, vectors X and Y are respectively trichotomized to yield two new vectors $TX=[tx(1), tx(2), \ldots, tx(L)]$ and $TY=[ty(1), ty(2), \ldots, ty(L)]$. The ASCI between X and Y, or ASCI(X,Y), which quantifies the morphological similarity between the two waveforms, are defined by the following formula:

$$ASCI(X, Y) = \frac{TX \circ TY}{\sqrt{TX \circ TX} \cdot \sqrt{TY \circ TY}}$$

Here, the symbol ∘ denotes the signed correlation product (SCP) of two trichotomized vectors, and is defined by the following formula:

$$TX \circ TY = \sum_{i=1}^{L} tx(i) \otimes ty(i)$$

Here, the symbol ⊗ denotes the signed correlation product (SCP) between two trichotomized scalars, and is defined by the following formula:

$$tx(i) \otimes ty(i) = \begin{cases} 1 & \text{if } tx(i) = ty(i) \\ -1 & \text{if } tx(i) \cdot ty(i) = -1 \\ 0 & \text{otherwise} \end{cases}$$

Figure 15A:
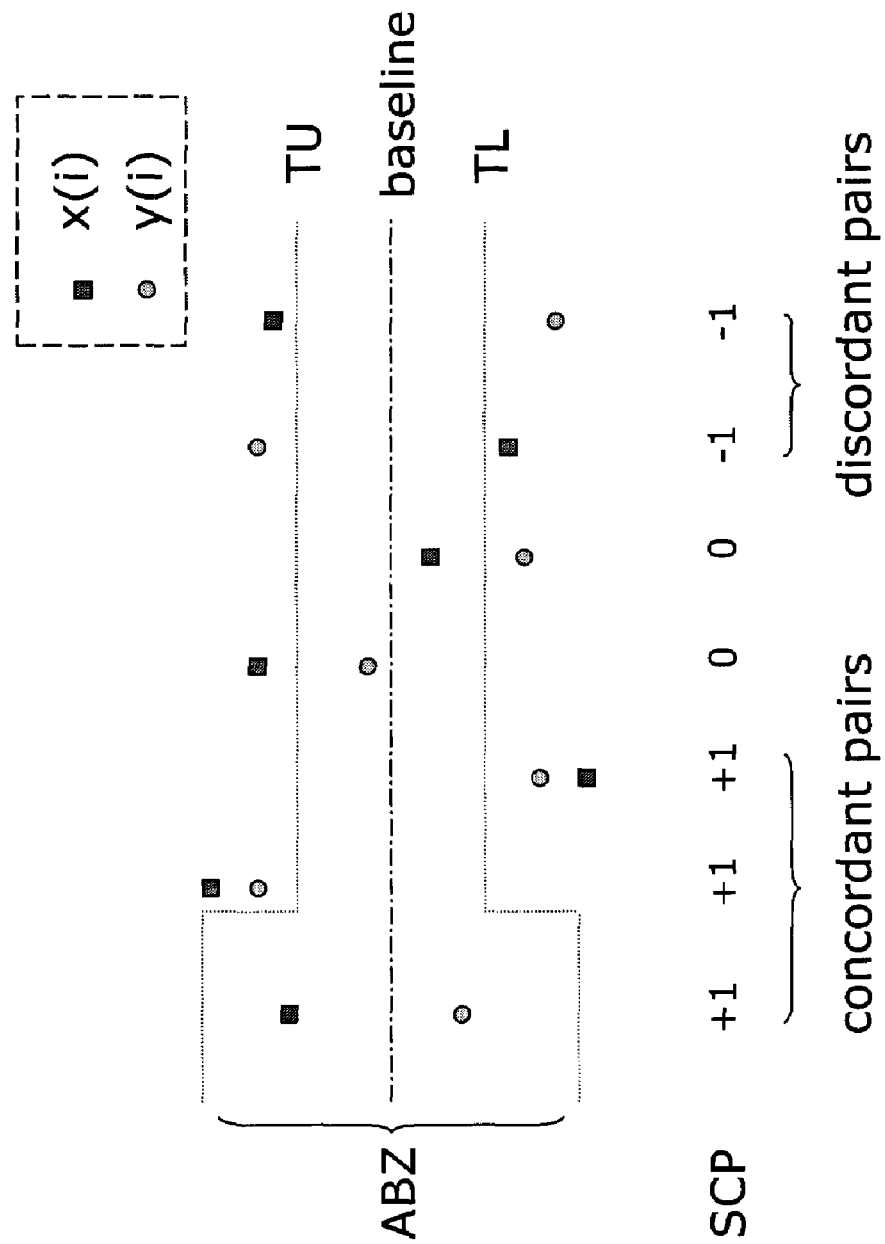
FIGS. 15a and 15b illustrate the concept of determining a signed correlation product (SCP) between a pair of samples.
Figure 15B:
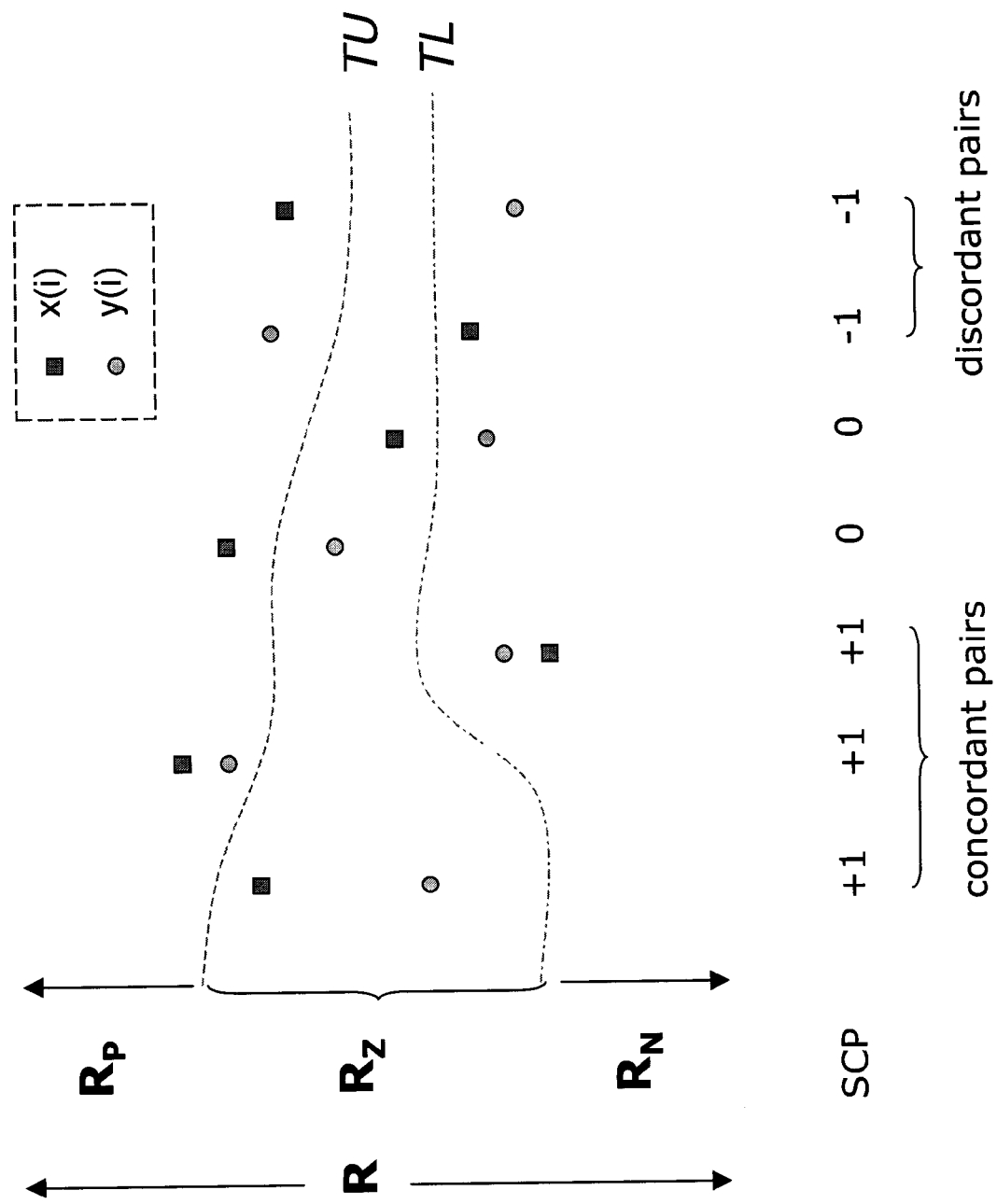

FIGS. 15a and 15b illustrate the concept of SCP between a pair of samples.

Accordingly, if $tx(i)=ty(i)$, their SCP is +1. In this case, the sample pair x(i) and y(i) are considered concordant, meaning that they have the same phase (amplitude sign), as exemplified by the first three sample pairs shown in FIGS. 15a and 15b. Specifically, if $tx(i)=ty(i)=+1$, then both samples are positive (above the positive threshold); if $tx(i)=ty(i)=-1$, then both samples are negative (below the negative threshold); if $tx(i)=ty(i)=0$, then both samples are within the adaptive baseline zone (ABZ).

On the other hand, if $tx(i) \cdot ty(i)=-1$, their SCP is −1. In this case, the sample pair x(i) and y(i) are considered discordant, meaning that they have the opposite phase, as exemplified by the last two sample pairs shown in FIGS. 15a and 15b. Specifically, it occurs if $tx(i)=+1$ and $ty(i)=-1$, or $tx(i)=-1$ and $ty(i)=+1$. In both cases, one sample is positive (above the positive threshold), and another sample is negative (below the negative threshold).

Otherwise, the case must be either $tx(i)=0$ and $ty(i) \neq 0$, or $tx(i) \neq 0$ and $ty(i)=0$, and their SCP is 0. In this case, the sample pair x(i) and y(i) are considered neither concordant, nor discordant, because one sample is within the adaptive baseline zone (ABZ), whereas the other sample is outside the ABZ (either positive or negative), as exemplified by the middle two sample pairs shown in FIG. 6.

According to the above definition, the SCP of two vectors (TX∘TY) is the sum of the SCP of all sample pairs tx(i) ⊗ ty(i), for $i=1 \ldots L$. Therefore, the SCP of two vectors will be contributed by each pair of concordant samples (+1), punished by each pair of discordant samples (−1), or not affected otherwise (neither concordant nor discordant sample pair).

In a special case when all sample pairs of two vectors are concordant, the SCP of these two vectors reaches maximum value L (the length of the vector). In another special case when all sample pairs of two vectors are discordant, the SCP of these two vectors reaches minimum value −L.

Therefore, for above defined TX and TY, it is obvious that TX∘TX=L and TY∘TY=L. Consequently, the formula for calculating ASCI(X,Y) defined above can be simplified to:

$$ASCI(X, Y) = \frac{TX \circ TY}{L}$$

Obviously, ASCI(X,Y) is a normalized index ranging from −1 to +1. If vectors X and Y have similar morphology, they will have more concordant sample pairs, and ASCI(X,Y) will approach +1. On the other hand, if vectors X and Y have different morphology, they will have fewer concordant sample pairs, and ASCI(X,Y) will be less. In a special case when X and Y have opposite phases, then ASCI(X,Y) will approach −1.

Therefore, ASCI(X,Y) provides a quantitative measure of the similarity between waveforms X and Y. The definition of ASCI is compatible to the conventional definition of Pearson's correlation coefficient, and they share the same properties (e.g., normalized from −1 to +1). However, the ASCI bears advantages over Pearson's correlation coefficient, due to at least two reasons.

First, the calculation of Pearson's correlation coefficient requires extensive floating-point operation including multiplication, division, and square root. On the other hand, the calculation of ASCI only requires comparison (trichotomization) and summation (SCP of two vectors). The normalization operation (divided by L) can be omitted because the ASCI will be mainly used for comparison with predefined/user-programmable threshold(s) to determine if two waveforms have similar morphology. For such purpose, the threshold(s) can be defined in the form of X-out-of-Y criterion, or by means of bit shifting of L. Therefore, the calculation of ASCI is computationally much more efficient, and can be easily implemented in firmware or hardware.

Second, although the Pearson's correlation coefficient can measure the phase similarity between two waveforms, it ignores the amplitude difference between the two waveforms. For example, the Pearson's correlation coefficient between vector X and vector Y=X/2 is 1.0, even though the amplitude of Y is only half of X. On the other hand, the calculation of ASCI takes amplitude information into consideration, because both waveforms are trichotomized based on the same ABZ, whose positive and negative threshold vectors are adaptive to the max amplitude of the template waveform. Therefore, a high ASCI value between two waveforms requires that they not only have consistent phase, but also have compatible amplitude.

According to this invention, for two waveforms X and Y, only the un-blanking portion of the waveforms are used to calculate the ASCI(X,Y). Specifically, for any sample in the blanking window of X, the corresponding sample pair are excluded from calculating the TX∘TY. Similarly, for any sample in the blanking window of Y, the corresponding sample pair are also excluded from calculating the TX∘TY. In other words, TX∘TY is calculated as the sum of tx(i) $\otimes$ ty(i), for i=1 . . . L, and neither x(i) nor y(i) is blanked. Denote L0 as the total number of sample pairs, in which both samples are un-blanked. Then effectively there are L0 pairs of samples contribute to the calculation of TX∘TY. Consequently, the ASCI(X,Y) is calculated by normalizing TX∘TY with L0, that is:

$$ASCI(X, Y) = \frac{TX \circ TY}{L0}$$

It is obvious that L0<L, and the value of L0 depends on the device parameter settings, such as in-channel blanking window, cross-channel blanking window, the VV delay, etc.

Figure 16:
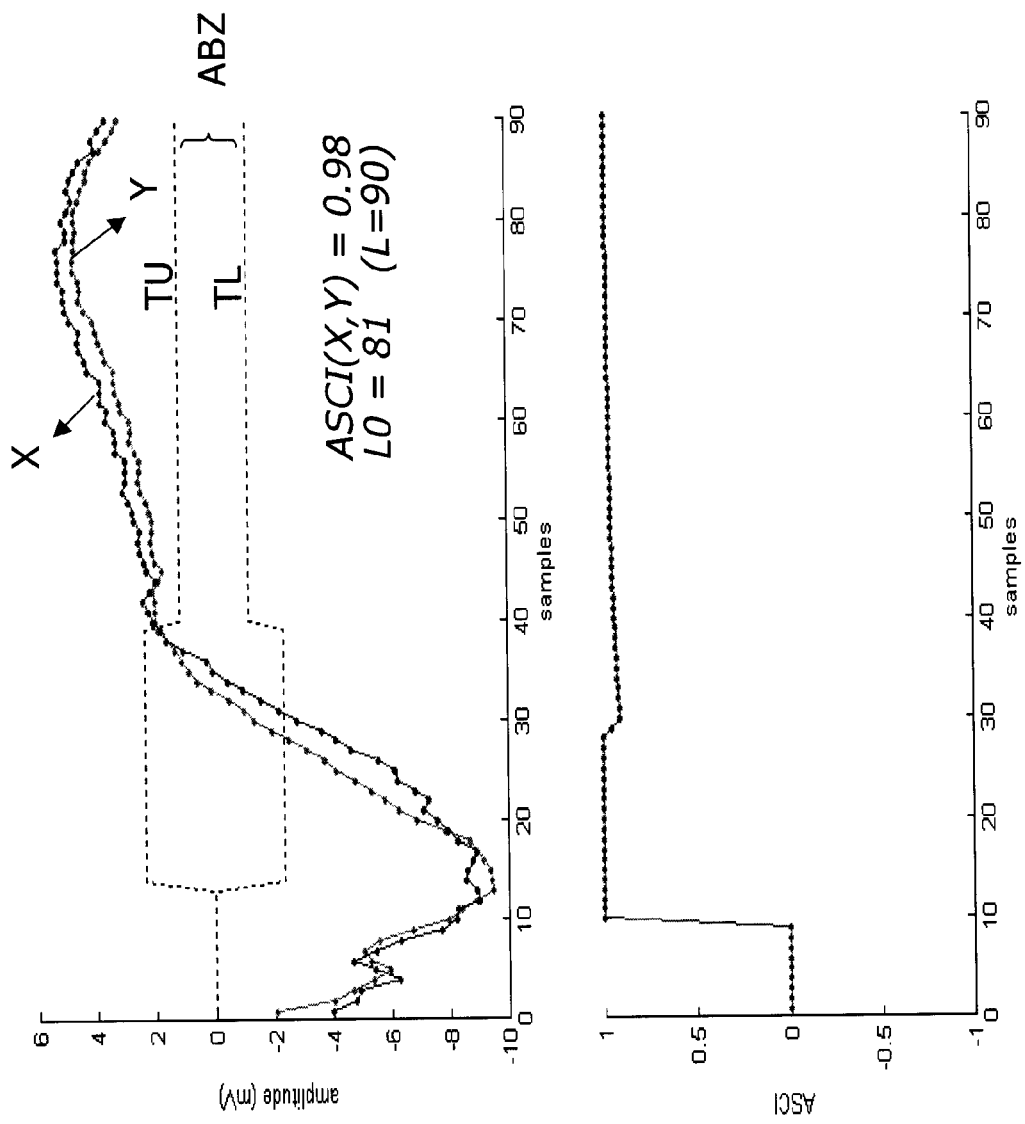
FIG. 16 shows an example of a captured waveform that has similar morphology to the template waveform, and is quantified by a high similarity index ASCI.

Refer to FIG. 16. The top panel shows an example of a captured waveform (X) that has similar morphology to the template waveform (Y). The length of each waveform (L) is 90 samples (350 ms at 256 Hz). The initial 9 samples (35 ms at 256 Hz) in each waveform are in the blanking windows. Thus there are L0=81 pairs of un-blanked samples that are used to calculate the ASCI(X,Y), which equals to 0.98 in this case. Assuming a predefined ASCI threshold of 0.75, then this above threshold ASCI(X,Y) indicates X and Y have highly consistent morphology, thus suggesting X a captured waveform.

Still refer to FIG. 16. In a typical embodiment, the ASCI (X,Y) is calculated by considering all un-blanked samples pairs (L0=81 in this example) of the waveforms. Yet in another embodiment, the ASCI between X and Y is further a function of p, that is ASCI(X,Y,p), where p is the count of un-blanked sample pairs. In other words, ASCI(X,Y) is continuously updated as any new pair of un-blanked samples are taken into consideration. As shown in the bottom panel, after the initial blanking window (9 sample pairs), the ASCI is calculated pair-by-pair, from the $10^{th}$ sample pair to the $90^{th}$ sample pair (p=1, 2, . . . , 81).

Therefore, according to this invention, the morphology comparison between two waveforms (thus the capture classification) can be made before the completion of the test waveform (i.e., reaching the full-length of the waveform L), based on the values of ASCI(X,Y,p) and p. For example, it can be determined that X and Y have consistent morphology if ASCI(X,Y,p) is greater than a predefined threshold, and meanwhile, counter p is also greater than another predefined value. Obviously, the comparison based on ASCI(X,Y,p) is more reliable for a larger p.

Figure 17:
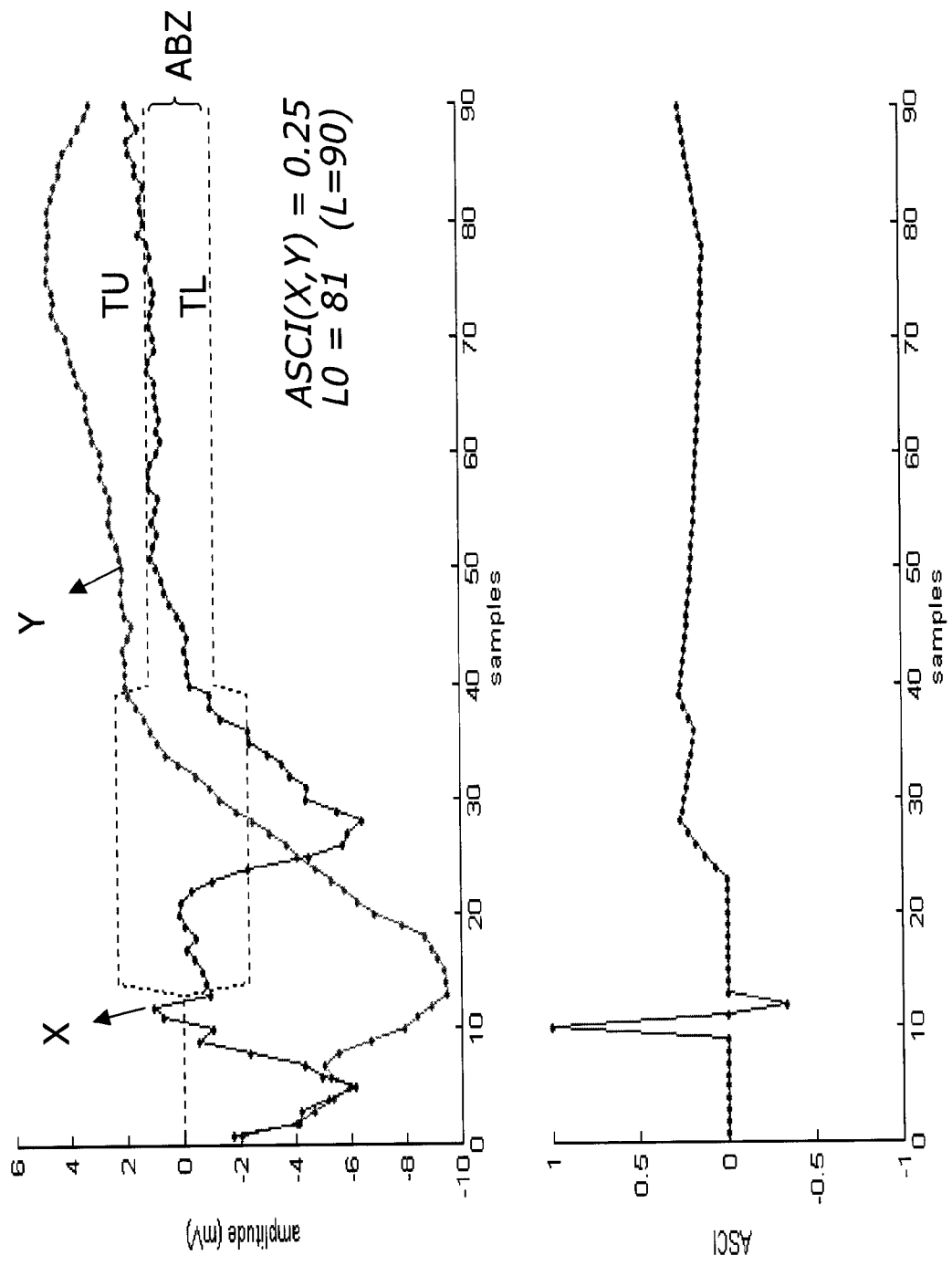
FIG. 17 shows an example of a non-captured waveform that has different morphology than the template waveform, and is quantified by a low similarity index ASCI.

Now refer to FIG. 17. The top panel shows an example of a non-captured waveform (X) that has different morphology than the template waveform (Y). The length of each waveform (L) is 90 samples (350 ms at 256 Hz). The initial 9 samples (35 ms at 256 Hz) in each waveform are in the blanking windows. Thus there are L0=81 pairs of un-blanked samples that are used to calculate the ASCI(X,Y), which equals to 0.25 in this case. Assuming a predefined ASCI threshold of 0.75, then this below threshold ASCI(X,Y) indicates X and Y have different morphology, suggesting X a non-captured waveform.

Still refer to FIG. 17. As described above, the ASCI between X and Y can be further calculated as a function of p, where p is the count of un-blanked sample pairs. As shown in the bottom panel, after the initial blanking window (9 sample pairs), the ASCI is calculated pair-by-pair, from the $10^{th}$ sample pair to the $90^{th}$ sample pair (p=1, 2, . . . , 81).

Similarly, the morphology comparison between two waveforms (thus the capture classification) can be made before the completion of the test waveform (i.e., reaching the full-length of the waveform L), based on the values of ASCI(X,Y,p) and p. For example, it can be determined that X and Y have different morphology if ASCI(X,Y,p) is less than a predefined threshold, and meanwhile, counter p is greater than another predefined value. Obviously, the comparison based on ASCI (X,Y,p) is more reliable for a larger p.

Implementation of ASCI

Figure 18:
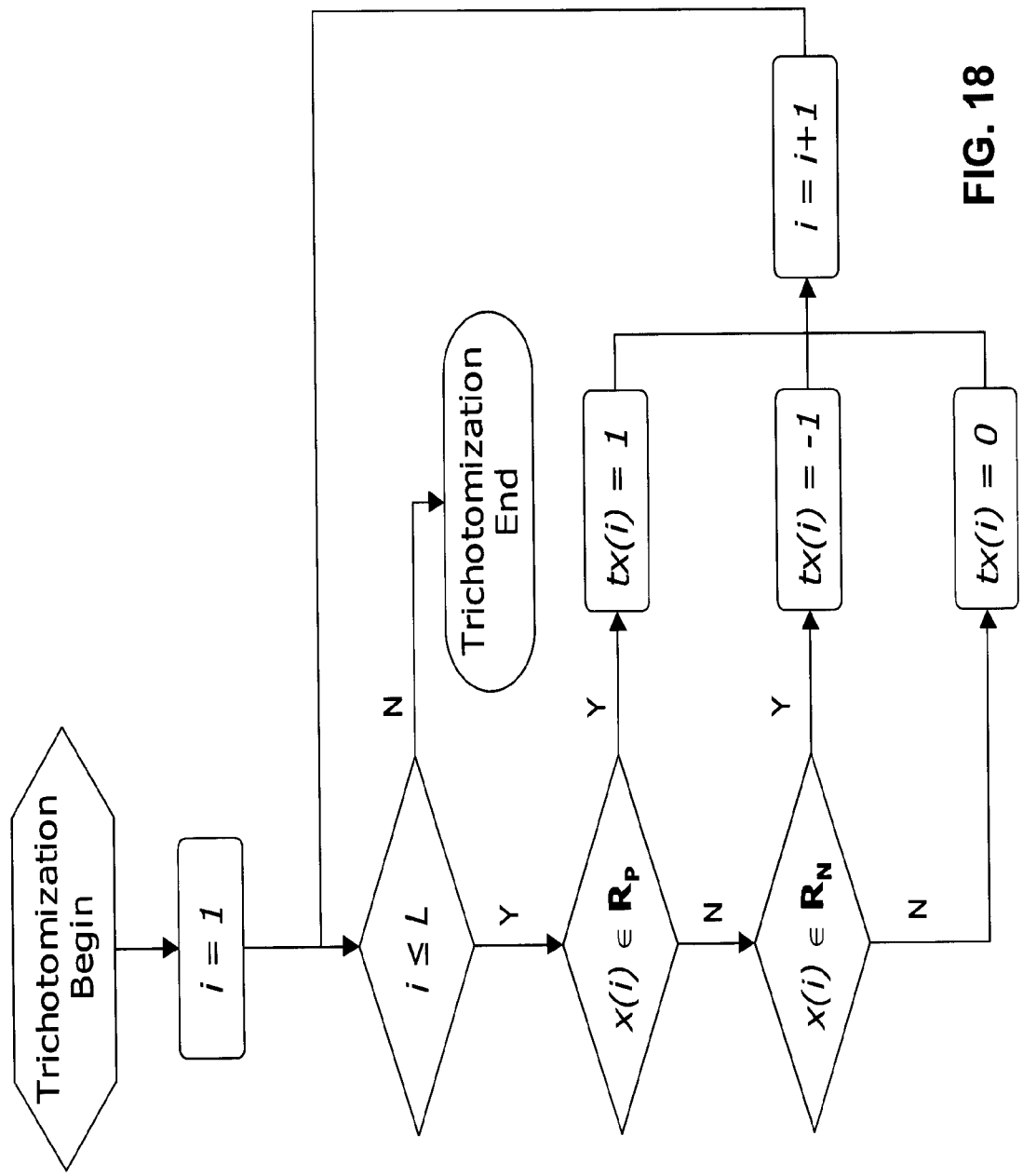
FIG. 18 shows the flowchart of alternative implementation of the signal trichotomization.

FIG. 18 shows the flowchart of alternative implementation of the signal trichotomization. As described above, the subspaces $R_P$, $R_Z$, and $R_N$ can be defined by multiple threshold vectors that are further adaptive to the template signal. Signal X is trichotomized by looping through all its samples x(i), for $1 \leq i \leq L$, then set output tx(i)=+1 if x(i) ∈ $R_P$, set tx(i)=−1 if x(i) ∈ $R_N$, or set tx(i)=0 otherwise, i.e., x(i) ∈ $R_Z$.

Figure 19:
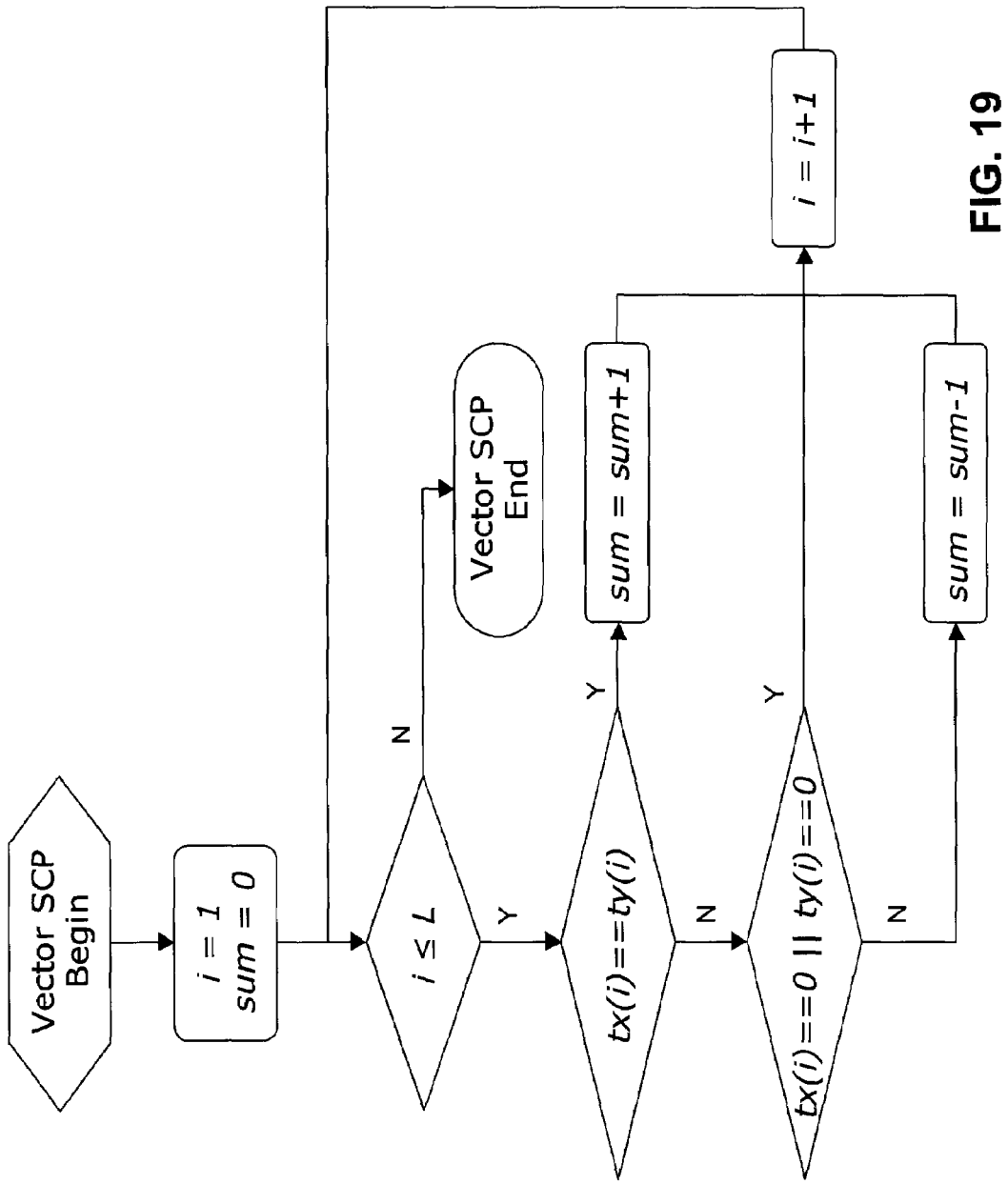
FIG. 19 shows the flowchart of an implementation of the signed correlation product (SCP) of two trichotomized vectors TX and TY.

FIG. 19 shows the flowchart of an implementation of the signed correlation product (SCP) of two trichotomized vectors TX and TY. After initialization of the SCP output sum=0, the procedure loops through all trichotomized sample pairs tx(i) and ty(i), for $1 \leq i \leq L$, then increase sum by 1 if tx(i)=ty(i), or no change to sum if either tx(i)=0 or ty(i)=0, or decrease sum by 1 otherwise. The ASCI(X,Y) is calculated as sum/L, and as discussed above, this final normalization step can be omitted in most cases.

It is obvious that calculation of ASCI can be easily implemented in hardware due to its computation efficiency, which is particularly desired for low-power devices.

Figure 20:
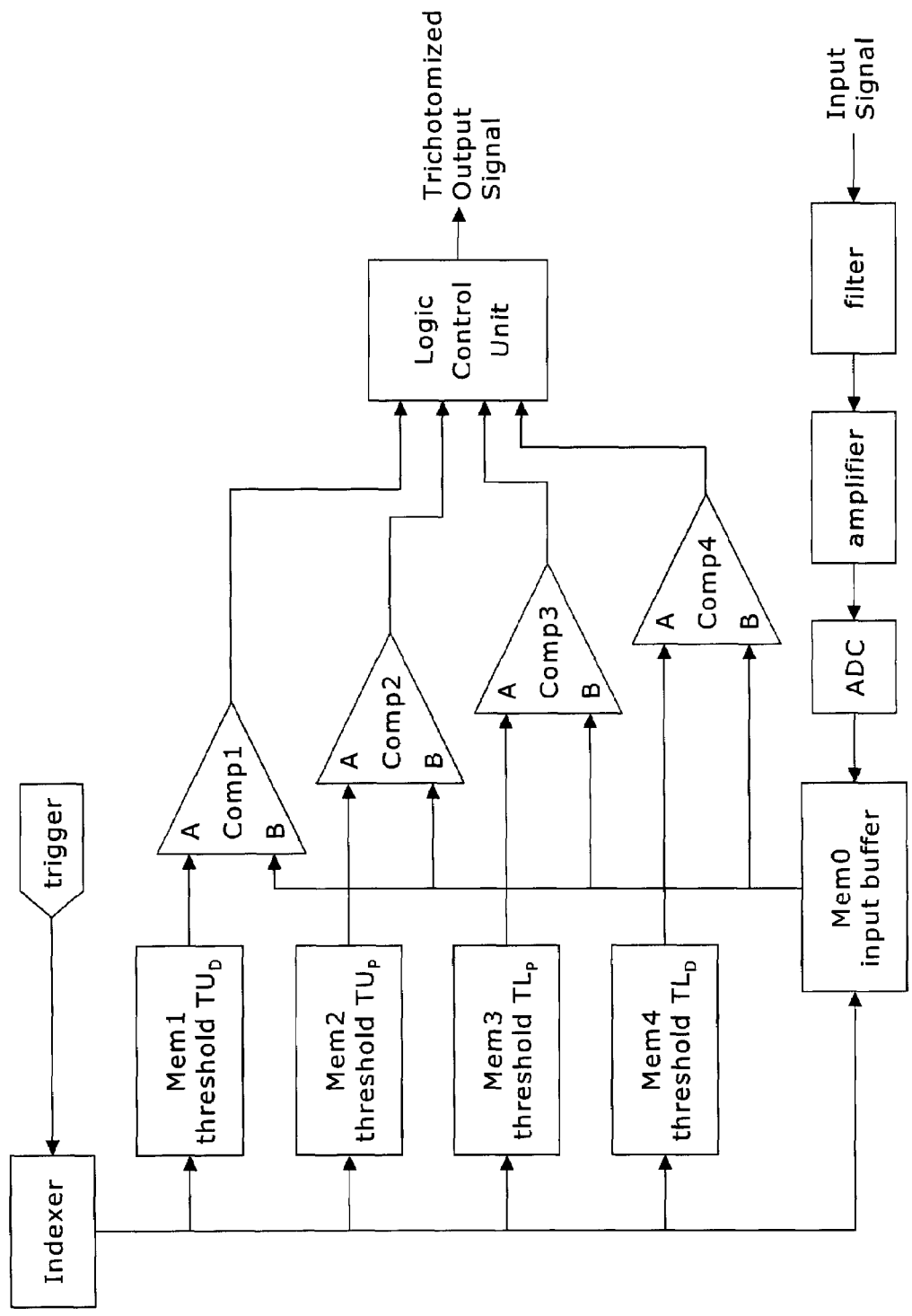
FIG. 20 shows a high-level block diagram for hardware implementation of the signal trichotomization using four threshold vectors as illustrated in FIG. 10.

FIG. 20 shows a high-level block diagram for hardware implementation of the signal trichotomization using four threshold vectors as illustrated in FIG. 10. The input signal is filtered, amplified, analog-to-digital converted, and then stored in an input memory buffer. The four threshold vectors, which are derived from the template signal, are stored in four different memory buffers and can be dynamically updated. Upon receiving a command trigger for evaluating the input signal (test signal), the indexer points to the first sample of the test signal stored in the input memory buffer, as well as the first sample of each threshold vector stored in each threshold memory buffer, then loops through all samples of the test signal and the threshold vectors. For each indexer output, the selected test signal sample is compared against four selected thresholds through four comparators. The outputs of the four comparators are then connected to the input ports of a logic control unit, which generates the trichotomized output signal.

As described in FIG. 10, the output is +1 if the input sample is higher than the proximal lower threshold (TLP) and lower than the proximal upper threshold (TUP), or −1 if the input sample is lower than the distal lower threshold (TLD) or higher than the distal upper threshold (TUD), or 0 otherwise.

Figure 21:
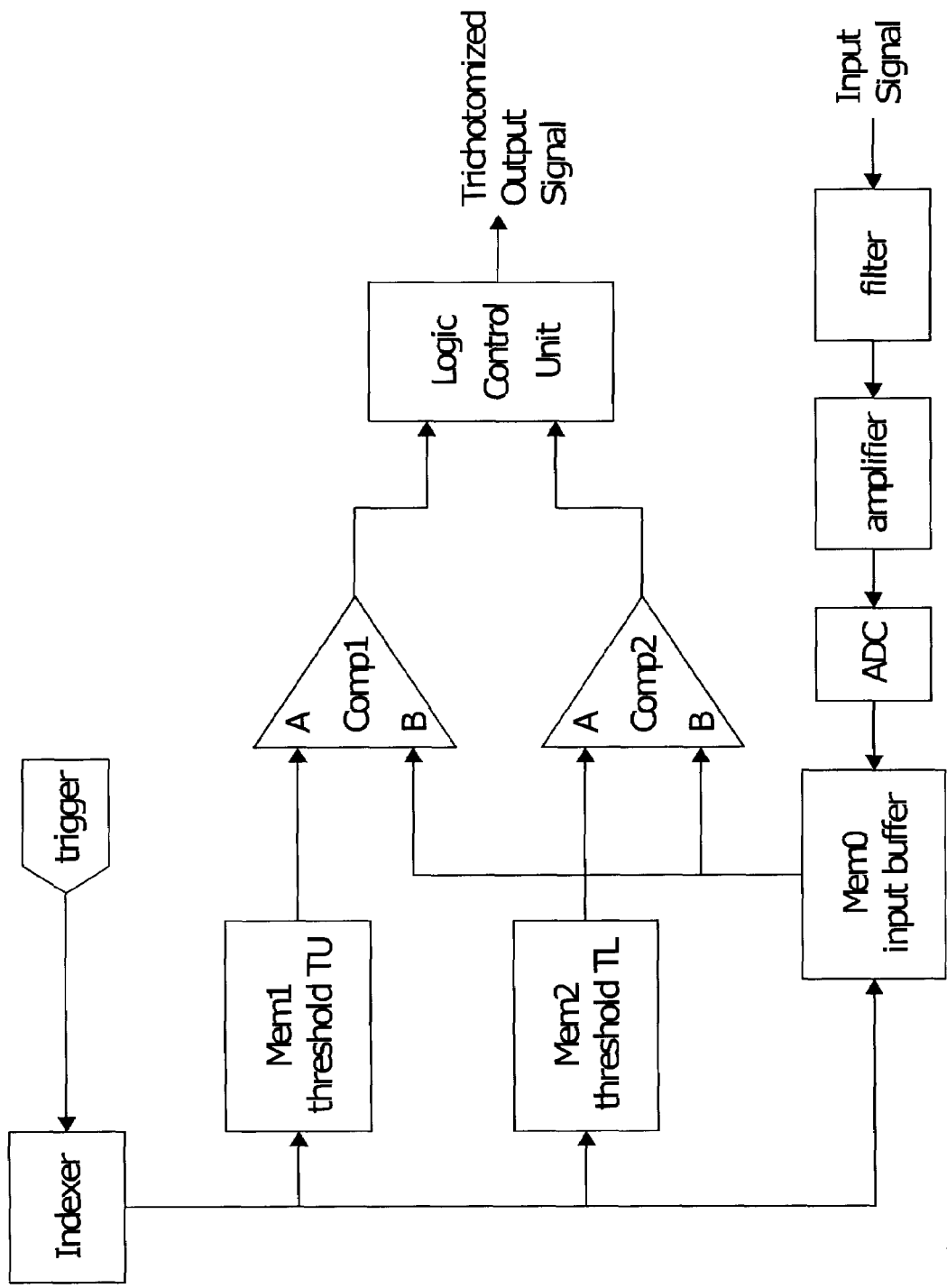
FIG. 21 shows another high-level block diagram for hardware implementation of the signal trichotomization using two threshold vectors as illustrated in FIG. 12.

FIG. 21 shows another high-level block diagram for hardware implementation of the signal trichotomization using two threshold vectors as illustrated in FIG. 12. Similarly, the input signal is filtered, amplified, analog-to-digital converted, and then stored in an input memory buffer. The two threshold vectors, which are derived from the template signal, are stored in two different memory buffers and can be dynamically updated. Upon receiving a command trigger for evaluating the input signal (test signal), the indexer points to the first sample of the test signal stored in the input memory buffer, as well as the first sample of each threshold vector stored in each threshold memory buffer, then loops through all samples of the test signal and the threshold vectors. For each indexer output, the selected test signal sample is compared against two selected thresholds through two comparators. The outputs of the two comparators are then connected to the input ports of a logic control unit, which generates the trichotomized output signal. As described in FIG. 12, the output is +1 if the input sample is higher than the upper threshold (TU), or −1 if the input sample is lower than the lower threshold (TL), or 0 otherwise.

Figure 22:
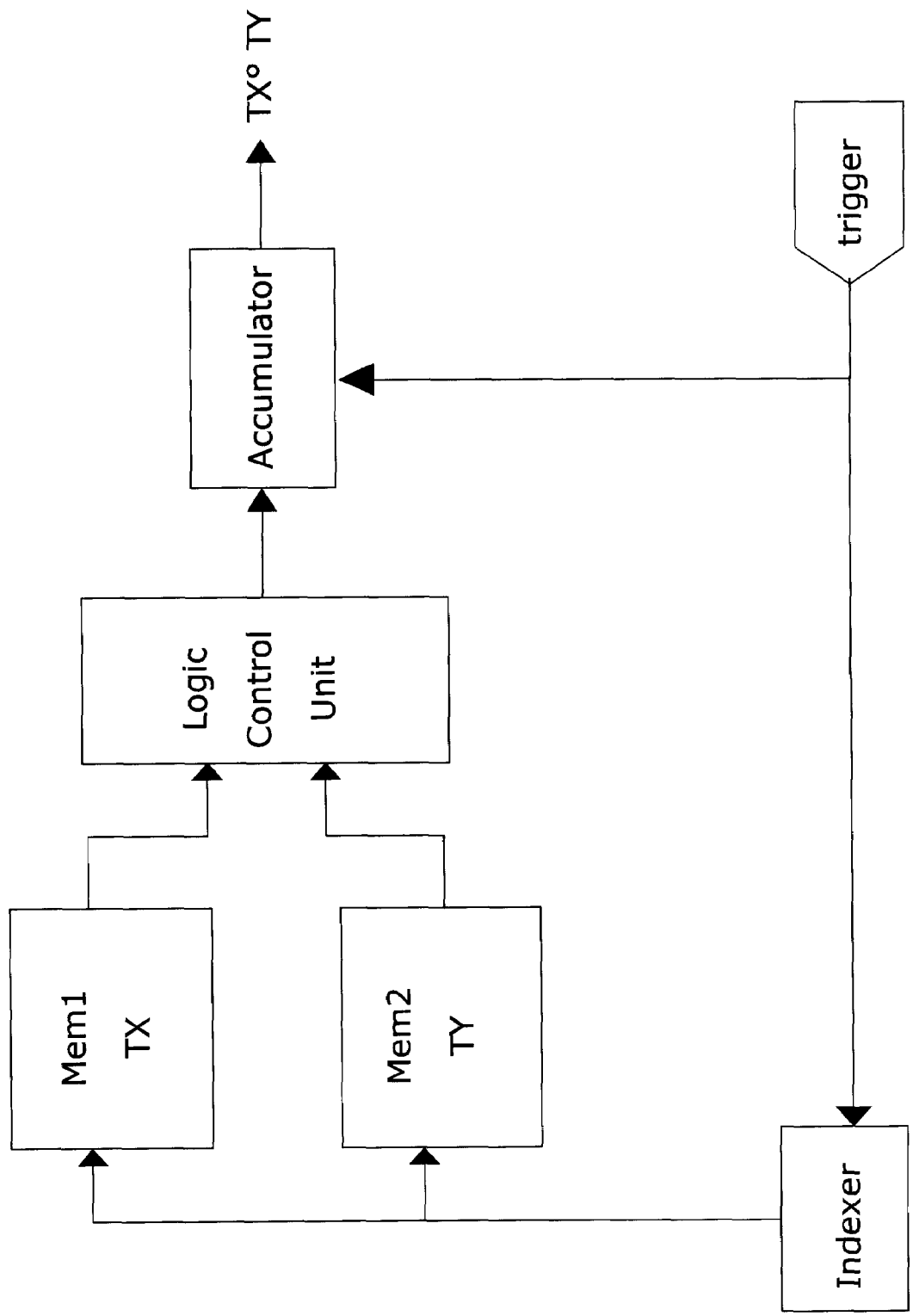
FIG. 22 shows a high-level block diagram for hardware implementation of the signed correlation product (SCP) of two trichotomized signals, which are respectively stored in two memory buffers.

FIG. 22 shows a high-level block diagram for hardware implementation of the signed correlation product (SCP) of two trichotomized signals, which are respectively stored in two memory buffers. Upon receiving a command trigger for evaluating the SCP of the two trichotomized signals, the accumulator is cleared, and the indexer points to the first sample of each trichotomized signal stored the respective memory buffer. Then the indexer loops through all samples of the trichotomized signals. For each indexer output, the selected pair of trichotomized samples are provided to the input ports of another logic control unit, which determines if the sample pair is concordant, discordant, or neither, and then generates output +1, −1, or 0, respectively. The output of the logic control unit is then connected to the accumulator module to generate the output of SCP between the two input signals. As discussed above, this final normalization step for calculating the ASCI can be omitted in most cases.

Automatic Capture Management

According to this invention, the implant device continuously monitors each pace in each chamber, and determines its capture status by evaluating the ASCI between the post-pace waveform and the corresponding template waveform. If the calculated ASCI is greater than a predefined/user-programmable threshold (preferably 0.75), than a capture status is classified; otherwise, a non-capture status is classified. As described above, if the calculated ASCI is greater than another predefined/user-programmable threshold (preferably 0.90), than running update of the template waveform can be made.

In one particular embodiment, the implant device always remains at the monitor state (MONITOR_STATE). The capture status of each pace in each chamber and the associated pacing parameters (e.g., pacing amplitude, pacing pulse width, pacing polarity) are logged into the device memory. The statistics in each chamber, for example, the percentage of captured paces and the percentage of non-captured paces, can then be calculated from the data log. Such statistics can then be interrogated through an external programmer and displayed to the user, or transmitted to the remote service center through wired or wireless Home Monitoring network.

In another particular embodiment, the implant device stays at the MONITOR_STATE, and continuously monitors the capture status of each pace in each chamber. If the device detects x non-capture paces out of y paces in a specific chamber, then loss-of-capture (LOC) is suspected, and the device automatically triggers a pacing threshold search to determine the pacing threshold in that chamber, and adjust the pacing energy (amplitude and/or pulse width) accordingly to ensure subsequent pacing capture.

Similarly, the capture status of each pace in each chamber and the associated pacing parameters (e.g., pacing amplitude, pacing pulse width, pacing polarity) are logged into the device memory. The statistics derived from these data, together with the threshold search results, can then be interrogated through an external programmer and displayed to the user, or transmitted to the remote service center through wired or wireless Home Monitoring network.

As well known in the art, the pacing threshold search is conducted by looping through a series of pacing energy levels, and to find the minimum energy that results in pacing capture. The pacing capture and non-capture classification during threshold search can be based on conventional evoked-potential analysis, such as the proprietary RV-ACC algorithm implemented in Philos II pacemakers, or by means of rhythm analysis, such as the RA-ATT algorithm disclosed in U.S. patent application Ser. No. 11/451,138 based on special device timing disclosed in U.S. patent application Ser. No. 11/560,009 all assigned to Biotronik GmbH. Evidently, the pacing capture and non-capture classification during threshold search can also use the method described above, that is, based on evaluation of the ASCI between test waveform and the template waveform.

Yet in another preferred embodiment, the implant device normally stays at the MONITOR_STATE, and continuously monitors the capture status of each pace in each chamber. When loss of capture (LOC) is suspected in one particular chamber, the device automatically enters one or more temporary states (see details below), to check if the detected non-capture status is caused by sub-threshold pacing, or caused by inappropriate device parameter setting, or caused by incidental events. If the sub-threshold pacing is confirmed, then LOC is declared, and the device automatically triggers a pacing threshold search to determine the pacing threshold in that chamber, and adjusts the pacing energy accordingly to ensure subsequent pacing capture. If the cause is inappropriate device parameter setting, then proper parameter adjustments are made to correct the problem. If the cause is due to incidental events (e.g., ectopic beat, noise, etc.), then no further action is required and the device returns to the MONITOR_STATE.

Similarly, the capture status of each pace in each chamber and the associated pacing parameters (e.g., pacing amplitude, pacing pulse width, pacing polarity) are logged into the device memory. The statistics derived from these data, together with the record of all actions and results (e.g., the threshold search results, the parameter changes), can then be interrogated through an external programmer and displayed to the user, or transmitted to the remote service center through wired or wireless Home Monitoring network.

Figure 23:
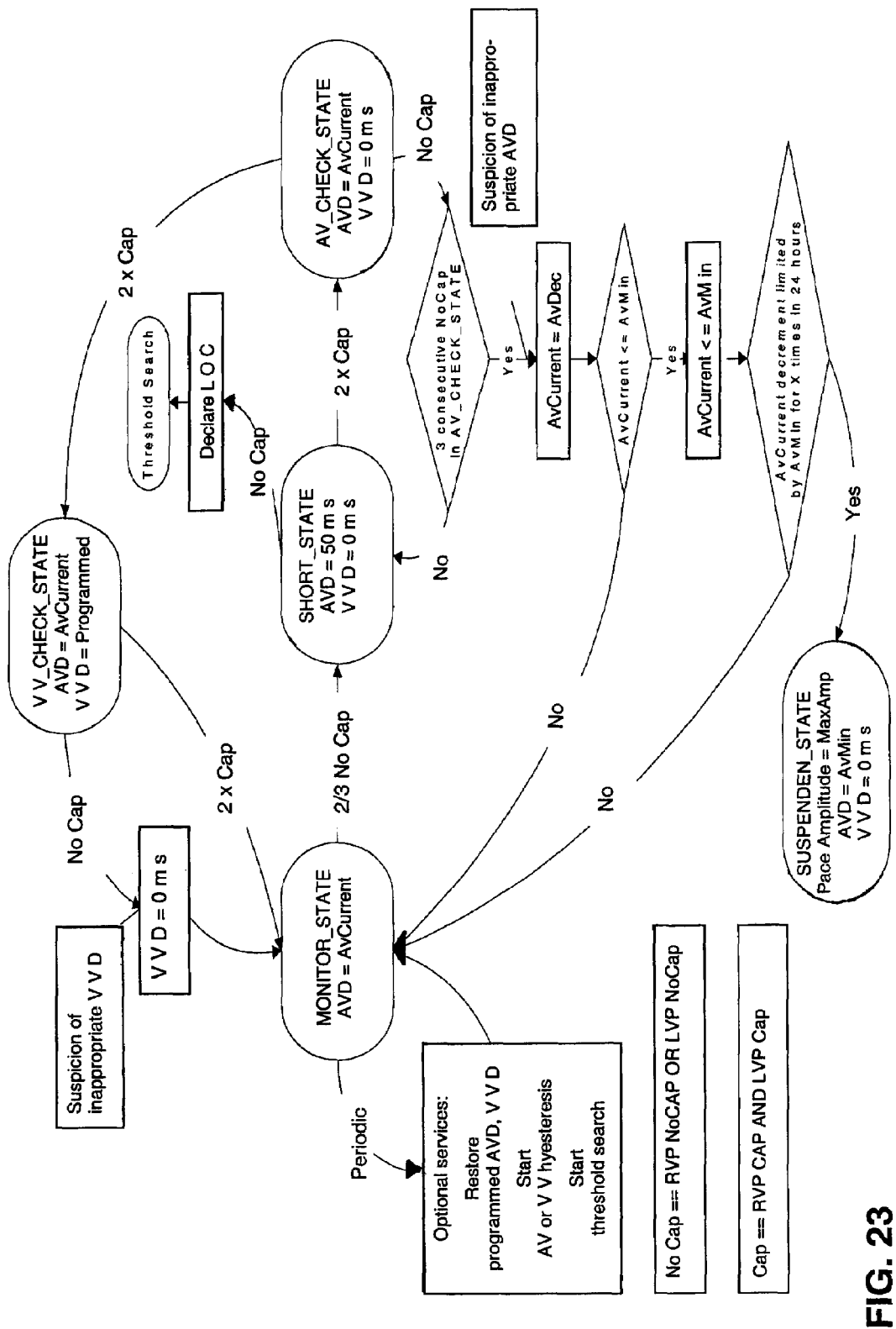
FIG. 23 shows the state diagram for an exemplarily embodiment of the automatic right ventricular and left ventricular capture management.

Now refer to FIG. 23, which shows an exemplary embodiment of the automatic capture management in bi-ventricular (right ventricular and left ventricular) pacing devices. Denote that capture is confirmed if both a right ventricular stimulation pulse (RVP) and a left ventricular stimulation pulse (LVP) are leading to capture (Cap), and denote non-capture is declared if either the right ventricular stimulation pulse (RVP) or the left ventricular stimulation pulse (LVP) has lead to non-capture (NoCap).

Still refer to FIG. 23. Device normally stays at the MONITOR_STATE. The AV delay (AVD) of the device may be fixed (programmed) or dynamic due to other device features, such as rate-adaptive AV delay, AV hysteresis, etc. Denote AVD=AvCurrent, to reflect the current AVD value. When x out of y (preferably 2 out of 3) RVP or LVP are classified as NoCap status, then the device transits to the SHORT_STATE by changing the device AVD from AvCurrent to a predefined short value (preferably 50 ms), and changing the device interventricular delay (VVD) to 0 ms (i.e., simultaneous RVP and LVP). By programming short AVD and VVD=0 ms, it is believed by the inventors that the likelihood of ventricular fusion, either due to antegrade AV conduction or due to interventricular conduction, is minimized.

Still refer to FIG. 23. If the NoCap status is detected in the SHORT_STATE, then LOC is declared, and the device automatically triggers a pacing threshold search to determine the pacing threshold in the suspected RV or LV chamber or both, and adjust the pacing energy accordingly to ensure subsequent pacing capture.

Still refer to FIG. 23. If in the SHORT_STATE, the device classifies Cap status for consecutive number of pace cycles (preferably 2), then the probability of sub-threshold pacing is very low. Accordingly, the device transits to the AV_CHECK_STATE, by restoring the AVD to AvCurrent (the AVD setting prior to the SHORT_STATE), while still maintaining VVD=0 ms. At AV_CHECK_STATE, it is believed by the inventors that the likelihood of ventricular fusion due to inter-ventricular conduction is minimized.

Still refer to FIG. 23. If the NoCap status is detected in the AV_CHECK_STATE, then device transits back to the SHORT_STATE for further testing. If such back-transition from AV_CHECK_STATE to SHORT_STATE occurs consecutively for multiple times (preferably 3), then it is believed by the inventors that the reason for the NoCap status is likely due to inappropriate AVD, which allows antegrade AV conduction that results in ventricular fusion. Accordingly, the device decrements AvCurrent by a programmed value (AvDec, e.g., 10 ms), under the condition that AvCurrent not being less than a predefined/user-programmed AVD lower limit (AvMin, e.g., 100 ms). Then, the device returns to the MONITOR_STATE, in which the AVD is updated to AvCurrent (less than the AVD prior to the SHORT_STATE if not limited by AvMin).

Still refer to FIG. 23. If the shortened AVD is still not short enough to solve the problem of ventricular fusion caused by antegrade AV conduction, then the device is expected to repeatedly go through the state loop described above, and further attempts to shorten the AVD, unless it is limited by the AVD lower limit (AvMin). If the attempts to shorten the AVD is limited by AvMin for multiple times (predefined/user-programmable, e.g., 4) within a day, then the device transits to the SUSPENDED_STATE, in which pacing amplitude is programmed to the predefined max amplitude, the AVD is fixed to AvMin, and VVD is fixed to 0 ms.

Still refer to FIG. 23. If in the AV_CHECK_STATE, the device classifies Cap status for consecutive number of pace cycles (preferably 2), then the possibility of ventricular fusion due to inappropriately long AVD is very low. Accordingly, the device transits to VV_CHECK_STATE, by restoring the VVD to programmed value (the VVD prior to the SHORT_STATE), while maintaining AVD=AvCurrent.

Still refer to FIG. 23. If NoCap status is detected in the VV_CHECK_STATE, then it is believed by the inventors that the reason for the NoCap status is likely due to inappropriate VVD, which allows interventricular conduction that results in ventricular fusion. Accordingly, the device changes VVD to 0 ms (i.e., simultaneous RVP and LVP), and returns to the MONITOR_STATE. On the other hand, if the device classifies Cap status for consecutive number of pace cycles (preferably 2) in the VV_CHECK_STATE, then the probability of ventricular fusion due to inappropriate VVD is very low. The reason for original NonCap status is likely due to incidental events (e.g., ectopic beat, noise, etc.), and the device returns to the MONITOR_STATE.

Still refer to FIG. 23. According to this invention, the device can be programmed to start the pacing threshold search periodically (e.g., every midnight) to determine the pacing threshold in the RV or LV chamber or both, and adjust the pacing energy accordingly to ensure subsequent pacing capture. In addition, the device can be programmed to restore the programmed AVD and VVD periodically (e.g., every midnight). This provides an opportunity for the device to re-try the programmed AVD and VVD, which might be inappropriate before but might become appropriate later. In another embodiment, the programmed AVD and VVD can be periodically tested through AV hysterisis or VV hysteresis. The programmed AVD and VVD are retained if they result in Cap status, otherwise, the AVD and VVD are not updated.

Figure 24:
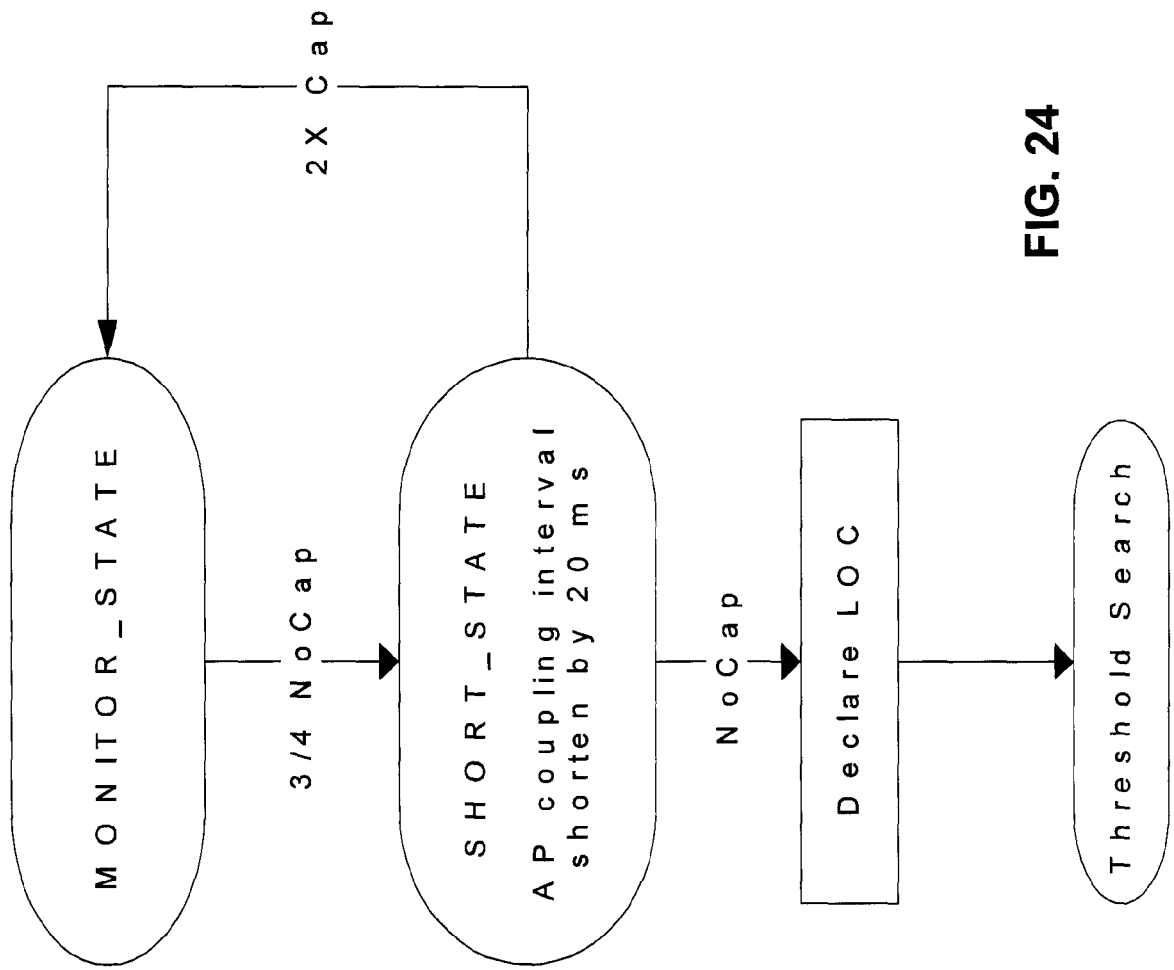
FIG. 24 shows the state diagram for an exemplarily embodiment of the automatic right atrial capture management.

Now refer to FIG. 24, which shows an exemplarily embodiment of an automatic right atrial (RAP) capture management. Denote Cap status as the RAP capture, and denote NoCap status as the RAP non-capture, determined by evaluating the ASCI between the post-pace waveform and the corresponding template waveform.

According to the present invention, the device normally stays at the MONITOR_STATE, and monitors the RAP capture status on a beat-by-beat basis. When x out of y (e.g., 3 out of 4) RAP are classified as NoCap status, then the device transits to the SHORT_STATE by temporarily shortening the AP coupling interval (or atrial escape interval), for example, to 20 ms less than the average atrial cycle length measured over multiple sensed/paced beats prior to the SHORT_STATE, to ensure atrial overdrive pacing.

Still refer to FIG. 24. If NoCap status is detected in the SHORT_STATE, then LOC is declared for RAP, and the device automatically triggers a pacing threshold search to determine the RA pacing threshold, and adjust the RAP energy accordingly to ensure subsequent pacing capture. On the other hand, if the device classifies Cap status for consecutive number of pace cycles (preferably 2), then the reason for original NonCap status is likely due to incidental events (e.g., intrinsic or ectopic atrial beat, noise, etc.), and the device returns to the MONITOR_STATE.

What is claimed is:
1. A medical device comprising:
a. at least one sensor for sampling a biological signal,
b. an evaluation unit connected to the sensor, wherein the evaluation unit receives samples of the biological signal and forms a waveform vector composed of the biological signal samples, and
c. a memory for storing at least two threshold vectors composed of boundary samples, the threshold vectors representing at least two boundaries related to the biological signal samples, the boundaries defining subspaces for the biological signal samples, wherein one threshold vector is an upper threshold vector composed of upper boundary samples and the other threshold vector is a lower threshold vector composed of lower bound- ary samples, wherein each lower boundary sample is less than or equal to the corresponding upper boundary sample, wherein the evaluation unit determines a similarity index (ASCI) by:
(1) comparing each of the biological signal samples of the waveform vector to corresponding boundary samples of the threshold vectors,
(2) creating trichotomized signal vectors dependent on the subspaces to which the biological signal samples correspond, and
(3) calculating the signed correlation product of two trichotomized signal vectors.

2. The medical device of claim 1 wherein the evaluation unit:
a. determines a positive threshold vector and a negative threshold vector which together define an adaptive threshold zone (ABZ);
b. determines a similarity index (ASCI) by:
(1) trichotomizing two waveform vectors based on the threshold vectors;
(2) calculating the signed correlation product between each sample pair of the two waveform vectors;
(3) calculating a signed correlation product between the two waveform vectors by summing the signed correlation products of all sample pairs; and
(4) normalizing the signed correlation product between the two waveform vectors by the total count of biological signal sample pairs.

3. The medical device of claim 2 wherein the evaluation unit trichotomizes a waveform vector by:
a. comparing each biological signal sample of the waveform vector to the threshold vectors;
b. setting the biological signal sample's trichotomized value to +1 if the biological signal sample is greater than the corresponding upper boundary sample;
c. setting the biological signal sample's trichotomized value to −1 if the biological signal sample is less than the corresponding lower boundary sample;
d. setting the biological signal sample's trichotomized value to 0 if the biological signal sample is less than or equal to the corresponding upper boundary sample, but greater than or equal to the corresponding lower boundary sample.

4. The medical device of claim 2 wherein the evaluation unit determines the signed correlation product of two trichotomized waveform vectors by:
a. taking one biological signal sample from a first vector and taking a corresponding biological signal sample from the second waveform vector, thus forming a biological signal sample pair,
b. setting the sample biological signal pair's signed correlation product output to +1 if:
(1) both biological signal samples are greater than the corresponding upper boundary sample, or
(2) both biological signal samples are less than the corresponding boundary sample, or
(3) both biological signal samples are greater than or equal to the corresponding lower boundary sample and less than or equal to the corresponding upper boundary sample;
c. setting the biological signal sample pair's signed correlation product output to −1 if
(1) one of the biological signal samples is greater than the corresponding upper boundary sample, and
(2) the other of the biological signal samples is less than the corresponding lower boundary sample;
d. setting the biological signal sample pair's signed correlation product output to 0 if:
(1) one of the biological signal samples is greater than or equal to the corresponding lower boundary sample and less than or equal than the corresponding upper boundary sample, and
(2) the other of the biological signal samples is either greater than the corresponding upper boundary sample or less than the corresponding lower boundary sample.

5. The medical device of claim 1 wherein the evaluation unit:
a. determines a template waveform vector, and
b. stores the template waveform vector for later determination of a similarity index (ASCI) for the template waveform vector and a test waveform vector.

6. The medical device of claim 5 further comprising:
a. at least one stimulation pulse generator connected to at least a stimulation electrode for delivering electric stimulation pulses to at least one chamber of a heart,
b. at least one sensing stage connected to an electrode for picking up electric potentials inside at least the chamber of a heart, the sensing stage being adapted to record at least a portion of an intracardiac electrogram (IEGM) in the heart chamber, and
c. a control unit connected to the stimulation pulse generator and the sensing stage, the control unit triggering generation of stimulation pulses by the stimulation pulse generator, wherein the evaluation unit:
(1) determines a capture template waveform vector from at least one IEGM portion representing an evoked response after successful stimulation of a heart chamber,
(2) stores the template waveform,
(3) generates a test waveform vector from an actual IEGM portion after a delivery of stimulation pulse to the heart chamber,
(4) determines a similarity index (ASCI) for the template waveform vector and the test waveform vector, and
(5) determines capture or loss of capture based on whether or not the similarity index thus determined for the test waveform exceeds a preset threshold value.

7. The medical device of claim 5 wherein:
a. the control unit:
(1) triggers generation of stimulation pulses with an overdrive stimulation rate exceeding an intrinsic heart rate as determined via the sensing stage to at least attempt triggering of a stimulation pulse before an intrinsic event occurs, and
(2) samples a post stimulation pulse intracardiac electrogram after each stimulation pulse generated with the overdrive stimulation rate, thus acquiring a sequence of biological signal samples forming a waveform vector,
b. the evaluation unit:
(1) collects waveform vectors for consecutive N cycles by sampling N post stimulation pulse intercardiac electrograms of the corresponding heart chamber;
(2) calculates the similarity index (ASCI) between each pair of biological signal samples of the collected waveform vectors; and
(3) generates the template waveform vector by averaging all N collected waveform vectors if the calculated ASCI of all N(N+1)/2 pairs are greater than a predefined threshold.

8. The medical device of claim 6 wherein the evaluation unit updates the template wave form vector on a beat-by-beat basis.

9. The medical device of claim 2 wherein the evaluation unit defines the upper threshold vector by:
   a. setting the boundary samples of the upper threshold vector and the lower threshold vector to 0 for a first post-stimulation pulse segment;
   b. setting the boundary samples of the upper threshold vector to one half of the largest sample of the post stimulation pulse intercardiac electrogram for the second post stimulation pulse segment; and
   c. setting the boundary samples of the upper threshold vector to one quarter of the largest sample of the post stimulation pulse intercardiac electrogram for the third post stimulation pulse segment.

10. The medical device of claim 9 wherein the evaluation unit defines the lower threshold vector by:
   a. setting the boundary samples of the lower threshold vector to 0 for a first post-stimulation pulse segment;
   b. setting the boundary samples of the lower threshold vector to a negative value of one half of the largest sample of the post stimulation pulse intercardiac electrogram for the second post stimulation pulse segment; and
   c. setting the boundary samples of the lower threshold vector to a negative value one quarter of the largest sample of the post stimulation pulse intercardiac electrogram for the third post stimulation pulse segment.

11. The medical device of claim 6 wherein the evaluation unit defines the upper threshold vector and the lower threshold vector sample-by-sample from a template threshold vector.

12. The medical device of claim 11 wherein the evaluation unit defines the upper threshold vector and the lower threshold vector by adding a positive offset value and a negative offset value, respectively, to some or each signal sample of the template waveform vector to thus generate an upper boundary sample and a lower boundary sample respectively.

13. The medical device of claim 11 wherein the evaluation unit defines the upper threshold vector and the lower threshold vector by scaling some or each signal sample of the template waveform vector by a factor greater than 1 and a factor less than one, respectively, to generate an upper boundary sample and a lower boundary sample respectively.

14. The medical device of claim 6 wherein the evaluation unit determines a capture status for a stimulation pulse by:
   a. calculating the similarity index (ASCI) between a test waveform vector and a corresponding template waveform vector, wherein the test waveform vector is generated after delivery of the stimulation pulse by sampling an according post stimulation pulse intracardiac electrogram; and
   b. confirming capture if the similarity index (ASCI) between the test waveform vector and the template waveform vector is greater than a predefined threshold.

15. The medical device of claim 14 wherein the evaluation unit updates the template waveform vector to the sum of:
   a. the template waveform vector prior to update, and scaled by 255/256, and
   b. the test waveform vector for which capture has been confirmed, scaled by 1/256.

16. The medical device of claim 6 wherein the evaluation unit ignores biological signal samples of template waveform vectors that correspond to a blanking window for the purpose of template vector update.

17. The medical device of claim 6 wherein the evaluation unit performs automatic capture management for more than one pacing configuration on a beat-by-beat basis, by:
   a. constructing a template waveform vector representing a sampled intracardiac electrogram after successful stimulation of a heart chamber for each pace configuration of the heart chamber;
   b. calculating the similarity index (ASCI) between a post-stimulation pulse test waveform and the corresponding template waveform;
   c. confirming capture if the similarity index (ASCI) between:
      (1) the test waveform vector, and
      (2) the template waveform vector for the pace configuration used for generating the test waveform vector, is greater than a threshold;
   d. declaring non-capture if the similarity index (ASCI) between:
      (1) the test waveform vector, and
      (2) the template waveform vector for the pace configuration used for generating the test waveform vector, is less than the threshold.

18. The medical device of claim 17 wherein the evaluation unit performs a right capture detection by:
   a. operating in MONITOR_STATE to monitor a capture status of each right atrial stimulation pulse by evaluating the similarity index (ASCI) between a post atrial stimulation pulse test waveform vector and a corresponding atrial stimulation template waveform vector;
   b. transiting from MONITOR_STATE to SHORT_STATE by temporarily shortening an atrial coupling interval (AAp interval or VAp interval), if 3 out of 4 right atrial stimulation pulses are classified as non-capture;
   c. declaring loss-of-capture if non-capture status is detected in the SHORT_STATE, and
      (1) triggering a pacing threshold search to determine the RA pacing threshold, and
      (2) adjusting a right atrial stimulation pulse strength accordingly to ensure subsequent right atrial capture; and
   d. returning to MONITOR_STATE if capture is confirmed in the SHORT_STATE.

19. The medical device of claim 17 wherein the evaluation unit performs an automatic capture management in a right ventricle and a left ventricle by:
   a. operating in MONITOR_STATE to monitor a capture status of each right ventricular stimulation pulse and left ventricular stimulation pulse by evaluating a similarity index (ASCI) between a post stimulation pulse test waveform vector and the corresponding template waveform vector, and:
      (1) confirming capture if capture is confirmed for both the right ventricular stimulation pulse and the left ventricular stimulation pulse, and
      (2) declaring non-capture if non-capture is declared for either the right ventricular stimulation pulse and the left ventricular stimulation pulse;
   b. transiting from MONITOR_STATE to SHORT_STATE by temporarily shortening an atrioventricular delay to 50 ms and setting an interventricular delay to 0 ms, if for 2 out 3 right ventricular stimulation pulses or left ventricular stimulation pulses non-capture has been declared;
   c. declaring loss-of-capture if non-capture is declared in the SHORT_STATE, and
      (1) triggering a capture threshold search to determine a minimum required stimulation pulse strength in the suspected right ventricle or left ventricle or both, and (2) adjusting the stimulation pulse strength accordingly to ensure subsequent capture of stimulation pulses;

d. transiting to AV_CHECK_STATUS by restoring an original atrioventricular delay while maintaining the interventricular delay of 0 ms, if capture is confirmed for 2 consecutive stimulated heart cycles in SHORT_STATE;

e. transiting back to SHORT_STATE if non-capture is declared in the AV_CHECK_STATE and such back-transition does not occur for 3 consecutive times;

f. decreasing the atrioventricular delay by a predefined interval if the state transition from AV_CHECK_STATE to SHORT_STATE occurs for 3 consecutive times;

g. limiting the decrement of the atrioventricular delay by a predefined minimum atrioventricular delay, and returning to the MONITOR_STATE;

h. transiting to SUSPENDED_STATE by programming a maximum right ventricular stimulation pulse amplitude and a maximum left ventricular stimulation pulse amplitude, a minimum atrioventricular delay, and an interventricular delay of 0 ms, if the attempts to shorten the atrioventricular delay is limited by the minimum atrioventricular delay for multiple times within a day;

i. transiting to VV_CHECK_STATE by restoring the programmed interventricular delay value, if capture is confirmed for 2 consecutive stimulated heart cycles in the AV_CHECK_STATE;

j. changing the interventricular delay to 0 ms if non-capture is declared in the VV_CHECK_STATE, and returning to the MONITOR_STATE;

k. returning to MONITOR_STATE if capture is confirmed for consecutive 2 pace cycles in the VV_CHECK_STATE;

l. triggering threshold search periodically to determine the capture threshold for the right ventricle or the left ventricle or both, and adjust the stimulation pulse strength accordingly to ensure subsequent capture stimulation pulses; and m. restoring the programmed atrioventricular delay and interventricular delay periodically, or testing the programmed atrioventricular delay and interventricular delay periodically, and restoring the programmed atrioventricular delay and interventricular delay only if they result in confirming capture.

* * * * *